United States Patent
Pinter et al.

(10) Patent No.: US 11,389,962 B2
(45) Date of Patent: Jul. 19, 2022

(54) TELEPRESENCE ROBOT SYSTEM THAT CAN BE ACCESSED BY A CELLULAR PHONE

(71) Applicant: INTOUCH TECHNOLOGIES, INC., Goleta, CA (US)

(72) Inventors: Marco Pinter, Santa Barbara, CA (US); Leon Miguel Medus, Bahia Blanca (AR); Daniel Steven Sanchez, Goleta, CA (US)

(73) Assignee: Teladoc Health, Inc., Purchase, NY (US)

( * ) Notice: Subject to any disclaimer, the term of this patent is extended or adjusted under 35 U.S.C. 154(b) by 0 days.

(21) Appl. No.: 16/505,359

(22) Filed: Jul. 8, 2019

(65) Prior Publication Data

US 2020/0101615 A1 Apr. 2, 2020

Related U.S. Application Data

(63) Continuation of application No. 12/785,791, filed on May 24, 2010, now Pat. No. 10,343,283.

(51) Int. Cl.
  *B25J 9/16* (2006.01)
  *B25J 11/00* (2006.01)
  (Continued)

(52) U.S. Cl.
  CPC ........... *B25J 9/1689* (2013.01); *B25J 11/009* (2013.01); *G16H 20/40* (2018.01); *G16H 40/67* (2018.01);
  (Continued)

(58) Field of Classification Search
  None
  See application file for complete search history.

(56) References Cited

U.S. PATENT DOCUMENTS

| 3,821,995 A | 7/1974 | Aghnides |
| 4,107,689 A | 8/1978 | Jellinek |

(Continued)

FOREIGN PATENT DOCUMENTS

| AU | 1216200 A | 5/2000 |
| CA | 2289697 A1 | 11/1998 |

(Continued)

OTHER PUBLICATIONS

Rajesh, Arumugan, et al., DAvinCi: A cloud computing framework for service robots, 2010 IEEE International Conference on Robotics and Automation, Anchorage Convention District, May 3-8, 2010, Anchorage, Alaska, USA (https://ieeexplore.ieee.org/stamp/stamp.jsp?tp=&arnumber=5509469) (hereinafter "Rajesh").*

(Continued)

*Primary Examiner* — Jean Paul Cass

(57) ABSTRACT

A robot system with a robot that has a camera, a monitor, a microphone and a speaker. A communication link can be established with the robot through a cellular phone. The link may include an audio only communication. Alternatively, the link may include audio and video communication between the cellular phone and the robot. The phone can transmit its resolution to the robot and cause the robot to transmit captured images at the phone resolution. The user can cause the robot to move through input on the cellular phone. For example, the phone may include an accelerometer that senses movement, and movement commands are then sent to the robot to cause a corresponding robot movement. The phone may have a touch screen that can be manipulated by the user to cause robot movement and/or camera zoom.

9 Claims, 17 Drawing Sheets

(51) Int. Cl.
 *G16H 20/40* (2018.01)
 *H04M 1/72415* (2021.01)
 *G16H 40/67* (2018.01)

(52) U.S. Cl.
 CPC .................. *H04M 1/72415* (2021.01); *G05B 2219/40174* (2013.01); *H04M 2250/12* (2013.01); *H04M 2250/22* (2013.01)

(56) References Cited

U.S. PATENT DOCUMENTS

| | | | |
|---|---|---|---|
| 4,213,182 A | 7/1980 | Eichelberger et al. | |
| 4,413,693 A | 11/1983 | Derby | |
| 4,471,354 A | 9/1984 | Smith | |
| 4,519,466 A | 5/1985 | Shiraishi | |
| 4,553,309 A | 11/1985 | Hess et al. | |
| 4,572,594 A | 2/1986 | Schwartz | |
| 4,625,274 A | 11/1986 | Schroeder | |
| 4,652,204 A | 3/1987 | Arnett | |
| 4,669,168 A | 6/1987 | Tamura et al. | |
| 4,679,152 A | 7/1987 | Perdue | |
| 4,697,278 A | 9/1987 | Fleischer | |
| 4,697,472 A | 10/1987 | Hiyane | |
| 4,709,265 A | 11/1987 | Silverman et al. | |
| 4,733,737 A | 3/1988 | Falamak | |
| 4,751,658 A | 6/1988 | Kadonoff et al. | |
| 4,766,581 A | 8/1988 | Korn et al. | |
| 4,777,416 A | 10/1988 | George, II et al. | |
| 4,797,557 A | 1/1989 | Ohman | |
| 4,803,625 A | 2/1989 | Fu et al. | |
| 4,847,764 A | 7/1989 | Halvorson | |
| 4,875,172 A | 10/1989 | Kanayama | |
| 4,878,501 A | 11/1989 | Shue | |
| 4,942,512 A | 7/1990 | Kohno | |
| 4,942,538 A | 7/1990 | Yuan et al. | |
| 4,953,159 A | 8/1990 | Hayden et al. | |
| 4,974,607 A | 12/1990 | Miwa | |
| 4,977,971 A | 12/1990 | Crane, III et al. | |
| 5,006,988 A | 4/1991 | Borenstein et al. | |
| 5,040,116 A | 8/1991 | Evans, Jr. et al. | |
| 5,051,906 A | 9/1991 | Evans, Jr. et al. | |
| 5,073,749 A | 12/1991 | Kanayama | |
| 5,084,828 A | 1/1992 | Kaufman et al. | |
| 5,130,794 A | 7/1992 | Ritchey | |
| 5,148,591 A | 9/1992 | Pryor | |
| 5,153,833 A | 10/1992 | Gordon et al. | |
| 5,155,684 A | 10/1992 | Burke et al. | |
| 5,157,491 A | 10/1992 | Kassatly | |
| 5,182,641 A | 1/1993 | Diner et al. | |
| 5,186,270 A | 2/1993 | West | |
| 5,193,143 A | 3/1993 | Kaemmerer et al. | |
| 5,217,453 A | 6/1993 | Wilk | |
| 5,220,263 A | 6/1993 | Onishi et al. | |
| 5,224,157 A | 6/1993 | Kamada et al. | |
| 5,230,023 A | 7/1993 | Nakano | |
| 5,231,693 A | 7/1993 | Backes et al. | |
| 5,236,432 A | 8/1993 | Matsen, III et al. | |
| 5,262,944 A | 11/1993 | Weisner et al. | |
| 5,305,427 A | 4/1994 | Nagata | |
| 5,315,287 A | 5/1994 | Sol | |
| 5,319,611 A | 6/1994 | Korba | |
| 5,341,242 A | 8/1994 | Gilboa et al. | |
| 5,341,459 A | 8/1994 | Backes | |
| 5,341,854 A | 8/1994 | Zezulka et al. | |
| 5,347,306 A | 9/1994 | Nitta | |
| 5,347,457 A | 9/1994 | Tanaka et al. | |
| 5,350,033 A | 9/1994 | Kraft | |
| 5,366,896 A | 11/1994 | Margrey et al. | |
| 5,374,879 A | 12/1994 | Pin et al. | |
| 5,375,195 A | 12/1994 | Johnston | |
| 5,400,068 A | 3/1995 | Ishida et al. | |
| 5,417,210 A | 5/1995 | Funda et al. | |
| 5,419,008 A | 5/1995 | West | |
| 5,436,542 A | 7/1995 | Petelin et al. | |
| 5,441,042 A | 8/1995 | Putman | |
| 5,441,047 A | 8/1995 | David et al. | |
| 5,442,728 A | 8/1995 | Kaufman et al. | |
| 5,462,051 A | 10/1995 | Oka et al. | |
| 5,486,853 A | 1/1996 | Baxter et al. | |
| 5,510,832 A | 4/1996 | Garcia | |
| 5,511,147 A | 4/1996 | Abdel-Malek | |
| 5,528,289 A | 6/1996 | Cortjens et al. | |
| 5,539,741 A | 7/1996 | Barraclough et al. | |
| 5,544,649 A | 8/1996 | David et al. | |
| 5,550,577 A | 8/1996 | Verbiest et al. | |
| 5,553,609 A | 9/1996 | Chen et al. | |
| 5,563,998 A | 10/1996 | Yaksich et al. | |
| 5,572,229 A | 11/1996 | Fisher | |
| 5,572,999 A | 11/1996 | Funda et al. | |
| 5,594,859 A | 1/1997 | Palmer et al. | |
| 5,600,573 A | 2/1997 | Hendricks et al. | |
| 5,617,539 A | 4/1997 | Ludwig et al. | |
| 5,619,341 A | 4/1997 | Auyeung et al. | |
| 5,623,679 A | 4/1997 | Rivette et al. | |
| 5,630,566 A | 5/1997 | Case | |
| 5,636,218 A | 6/1997 | Ishikawa et al. | |
| 5,652,849 A | 7/1997 | Conway et al. | |
| 5,657,246 A | 8/1997 | Hogan et al. | |
| 5,659,779 A | 8/1997 | Laird et al. | |
| 5,673,082 A | 9/1997 | Wells et al. | |
| 5,675,229 A | 10/1997 | Thorne | |
| 5,682,199 A | 10/1997 | Lankford | |
| 5,684,695 A | 11/1997 | Bauer | |
| 5,701,904 A | 12/1997 | Simmons et al. | |
| 5,734,805 A | 3/1998 | Isensee et al. | |
| 5,739,657 A | 4/1998 | Takayama et al. | |
| 5,748,629 A | 5/1998 | Caldara et al. | |
| 5,749,058 A | 5/1998 | Hashimoto | |
| 5,749,362 A | 5/1998 | Funda et al. | |
| 5,754,631 A | 5/1998 | Cave | |
| 5,758,079 A | 5/1998 | Ludwig et al. | |
| 5,762,458 A | 6/1998 | Wang et al. | |
| 5,764,731 A | 6/1998 | Yablon | |
| 5,767,897 A | 6/1998 | Howell | |
| 5,786,846 A | 7/1998 | Hiroaki | |
| 5,787,545 A | 8/1998 | Colens | |
| 5,793,365 A | 8/1998 | Tang et al. | |
| 5,801,755 A | 9/1998 | Echerer | |
| 5,802,494 A | 9/1998 | Kuno | |
| 5,836,872 A | 11/1998 | Kenet et al. | |
| 5,838,575 A | 11/1998 | Lion | |
| 5,844,599 A | 12/1998 | Hildin | |
| 5,857,534 A | 1/1999 | DeVault et al. | |
| 5,867,494 A | 2/1999 | Krishnaswamy et al. | |
| 5,867,653 A | 2/1999 | Aras et al. | |
| 5,871,451 A | 2/1999 | Unger et al. | |
| 5,872,922 A | 2/1999 | Hogan et al. | |
| 5,876,325 A | 3/1999 | Mizuno et al. | |
| 5,911,036 A | 6/1999 | Wright et al. | |
| 5,917,958 A | 6/1999 | Nunally et al. | |
| 5,927,423 A | 7/1999 | Wada et al. | |
| 5,949,758 A | 9/1999 | Kober | |
| 5,954,692 A | 9/1999 | Smith et al. | |
| 5,959,423 A | 9/1999 | Nakanishi et al. | |
| 5,961,446 A | 10/1999 | Beller et al. | |
| 5,966,130 A | 10/1999 | Benman, Jr. | |
| 5,973,724 A | 10/1999 | Riddle | |
| 5,974,446 A | 10/1999 | Sonnenreich et al. | |
| 5,983,263 A | 11/1999 | Rothrock et al. | |
| 5,995,119 A | 11/1999 | Cosatto et al. | |
| 5,995,884 A | 11/1999 | Mien et al. | |
| 5,999,977 A | 12/1999 | Riddle | |
| 6,006,946 A | 12/1999 | Williams et al. | |
| 6,031,845 A | 2/2000 | Walding | |
| 6,036,812 A | 3/2000 | Williams et al. | |
| 6,047,259 A | 4/2000 | Campbell et al. | |
| 6,091,219 A | 7/2000 | Maruo et al. | |
| 6,113,343 A | 9/2000 | Goldenberg et al. | |
| 6,133,944 A | 10/2000 | Braun et al. | |
| 6,135,228 A | 10/2000 | Asada et al. | |
| 6,148,100 A | 11/2000 | Anderson et al. | |
| 6,160,582 A | 12/2000 | Hill | |
| 6,170,929 B1 | 1/2001 | Wilson et al. | |
| 6,175,779 B1 | 1/2001 | Barrett | |

(56) References Cited

U.S. PATENT DOCUMENTS

| | | |
|---|---|---|
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,292,714 B1 | 9/2001 | Okabayashi |
| 6,304,050 B1 | 10/2001 | Skaar et al. |
| 6,314,631 B1 | 11/2001 | Pryor |
| 6,317,652 B1 | 11/2001 | Osada |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,411,055 B1 | 6/2002 | Fujita et al. |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,445,964 B1 | 9/2002 | White et al. |
| 6,449,762 B1 | 9/2002 | McElvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury, Jr. et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,667,592 B2 | 12/2003 | Jacobs et al. |
| 6,674,259 B1 | 1/2004 | Norman et al. |
| 6,684,129 B2 | 1/2004 | Salisbury, Jr. et al. |
| 6,691,000 B2 | 2/2004 | Nagai et al. |
| 6,693,585 B1 | 2/2004 | MacLeod |
| 6,710,797 B1 | 3/2004 | McNelley et al. |
| 6,724,823 B2 | 4/2004 | Rovati et al. |
| 6,728,599 B2 | 4/2004 | Wright et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe et al. |
| 6,957,712 B2 | 10/2005 | Song et al. |
| 6,958,706 B2 | 10/2005 | Chaco et al. |
| 6,965,394 B2 | 11/2005 | Gulla et al. |
| 6,990,112 B1 | 1/2006 | Brent et al. |
| 6,995,664 B1 | 2/2006 | Darling |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |

(56) References Cited

U.S. PATENT DOCUMENTS

| | | | |
|---|---|---|---|
| 7,155,306 B2 | 12/2006 | Haitin et al. | |
| 7,156,809 B2 | 1/2007 | Quy | |
| 7,158,859 B2 | 1/2007 | Wang et al. | |
| 7,158,860 B2 | 1/2007 | Wang et al. | |
| 7,158,861 B2 | 1/2007 | Wang et al. | |
| 7,161,322 B2 | 1/2007 | Wang et al. | |
| 7,162,338 B2 | 1/2007 | Goncalves et al. | |
| 7,164,969 B2 | 1/2007 | Wang et al. | |
| 7,164,970 B2 | 1/2007 | Wang et al. | |
| 7,167,448 B2 | 1/2007 | Wookey et al. | |
| 7,171,286 B2 | 1/2007 | Wang et al. | |
| 7,174,238 B1 | 2/2007 | Zweig | |
| 7,181,455 B2 | 2/2007 | Wookey et al. | |
| 7,184,559 B2 | 2/2007 | Jouppi | |
| 7,188,000 B2 | 3/2007 | Chiappetta et al. | |
| 7,199,790 B2 | 4/2007 | Rosenberg et al. | |
| 7,202,851 B2 | 4/2007 | Cunningham et al. | |
| 7,206,627 B2 | 4/2007 | Abovitz et al. | |
| 7,215,786 B2 | 5/2007 | Nakadai et al. | |
| 7,219,364 B2 | 5/2007 | Bolle et al. | |
| 7,222,000 B2 | 5/2007 | Wang et al. | |
| 7,227,334 B2 | 6/2007 | Yang et al. | |
| 7,256,708 B2 | 8/2007 | Rosenfeld et al. | |
| 7,262,573 B2 | 8/2007 | Wang et al. | |
| 7,272,572 B1* | 9/2007 | Pienkos | G06Q 50/184 |
| | | | 705/26.1 |
| 7,283,153 B2 | 10/2007 | Provost et al. | |
| 7,289,883 B2 | 10/2007 | Wang et al. | |
| 7,292,257 B2 | 11/2007 | Kang et al. | |
| 7,292,912 B2 | 11/2007 | Wang et al. | |
| 7,305,114 B2 | 12/2007 | Wolff et al. | |
| 7,317,685 B1 | 1/2008 | Flott et al. | |
| 7,321,807 B2 | 1/2008 | Laski | |
| 7,332,890 B2 | 2/2008 | Cohen et al. | |
| 7,333,642 B2 | 2/2008 | Green | |
| 7,346,429 B2 | 3/2008 | Goldenberg et al. | |
| 7,352,153 B2 | 4/2008 | Yan | |
| 7,363,121 B1 | 4/2008 | Chen et al. | |
| 7,382,399 B1 | 6/2008 | McCall et al. | |
| 7,386,730 B2 | 6/2008 | Uchikubo | |
| 7,391,432 B2 | 6/2008 | Terada | |
| 7,400,578 B2 | 7/2008 | Guthrie et al. | |
| 7,404,140 B2 | 7/2008 | O'rourke | |
| 7,421,470 B2 | 9/2008 | Ludwig et al. | |
| 7,430,209 B2 | 9/2008 | Porter | |
| 7,432,949 B2 | 10/2008 | Remy et al. | |
| 7,433,921 B2 | 10/2008 | Ludwig et al. | |
| 7,441,953 B2 | 10/2008 | Banks | |
| 7,467,211 B1 | 12/2008 | Herman et al. | |
| 7,483,867 B2 | 1/2009 | Ansari et al. | |
| 7,492,731 B2 | 2/2009 | Hagendorf | |
| 7,510,428 B2 | 3/2009 | Obata et al. | |
| 7,523,069 B1 | 4/2009 | Friedl et al. | |
| 7,525,281 B2 | 4/2009 | Koyanagi et al. | |
| 7,535,486 B2 | 5/2009 | Motomura et al. | |
| 7,557,758 B2 | 7/2009 | Rofougaran | |
| 7,587,260 B2 | 9/2009 | Bruemmer et al. | |
| 7,587,512 B2 | 9/2009 | Ta et al. | |
| 7,590,060 B2 | 9/2009 | Miceli | |
| 7,593,030 B2 | 9/2009 | Wang et al. | |
| 7,599,290 B2 | 10/2009 | Dos Remedios et al. | |
| 7,624,166 B2 | 11/2009 | Foote et al. | |
| 7,630,314 B2 | 12/2009 | Dos Remedios et al. | |
| 7,631,833 B1 | 12/2009 | Ghaleb et al. | |
| 7,643,051 B2 | 1/2010 | Sandberg et al. | |
| 7,647,320 B2 | 1/2010 | Mok et al. | |
| 7,657,560 B1 | 2/2010 | DiRienzo | |
| 7,680,038 B1 | 3/2010 | Gourlay | |
| 7,688,306 B2* | 3/2010 | Wehrenberg | G06F 3/165 |
| | | | 345/157 |
| 7,693,757 B2 | 4/2010 | Zimmerman | |
| 7,698,432 B2 | 4/2010 | Short et al. | |
| 7,703,113 B2 | 4/2010 | Dawson | |
| 7,719,229 B2 | 5/2010 | Kaneko et al. | |
| 7,737,993 B2 | 6/2010 | Kaasila et al. | |
| 7,739,383 B1 | 6/2010 | Short et al. | |
| 7,756,614 B2 | 7/2010 | Jouppi | |
| 7,761,185 B2 | 7/2010 | Wang et al. | |
| 7,769,492 B2 | 8/2010 | Wang et al. | |
| 7,769,705 B1 | 8/2010 | Luechtefeld | |
| 7,774,158 B2 | 8/2010 | Domingues et al. | |
| 7,813,836 B2 | 10/2010 | Wang et al. | |
| 7,831,575 B2 | 11/2010 | Trossell et al. | |
| 7,835,775 B2 | 11/2010 | Sawayama et al. | |
| 7,860,680 B2 | 12/2010 | Arms et al. | |
| 7,861,366 B2 | 1/2011 | Hahm et al. | |
| 7,885,822 B2 | 2/2011 | Akers et al. | |
| 7,890,382 B2 | 2/2011 | Robb et al. | |
| 7,912,583 B2 | 3/2011 | Gutmann et al. | |
| RE42,288 E | 4/2011 | Degioanni | |
| 7,924,323 B2 | 4/2011 | Walker et al. | |
| 7,949,616 B2 | 5/2011 | Levy et al. | |
| 7,956,894 B2 | 6/2011 | Akers et al. | |
| 7,957,837 B2 | 6/2011 | Ziegler et al. | |
| 7,982,763 B2 | 7/2011 | King | |
| 7,982,769 B2 | 7/2011 | Jenkins et al. | |
| 7,987,069 B2 | 7/2011 | Rodgers et al. | |
| 8,010,993 B1* | 8/2011 | Bartholomay | H04L 63/20 |
| | | | 726/1 |
| 8,027,937 B1* | 9/2011 | Bartholomay | H04L 41/5041 |
| | | | 706/47 |
| 8,066,379 B2* | 11/2011 | Lalley | G09B 9/003 |
| | | | 345/32 |
| 8,077,963 B2 | 12/2011 | Wang et al. | |
| 8,116,910 B2 | 2/2012 | Walters et al. | |
| 8,126,960 B2 | 2/2012 | Obradovich et al. | |
| 8,170,241 B2 | 5/2012 | Roe et al. | |
| 8,179,418 B2 | 5/2012 | Wright et al. | |
| 8,180,486 B2 | 5/2012 | Saito et al. | |
| 8,209,051 B2 | 6/2012 | Wang et al. | |
| 8,212,533 B2 | 7/2012 | Ota | |
| 8,265,793 B2 | 9/2012 | Cross et al. | |
| 8,287,522 B2 | 10/2012 | Moses et al. | |
| 8,292,807 B2 | 10/2012 | Perkins et al. | |
| 8,320,534 B2 | 11/2012 | Kim et al. | |
| 8,340,654 B2 | 12/2012 | Bratton et al. | |
| 8,340,819 B2 | 12/2012 | Mangaser et al. | |
| 8,348,675 B2 | 1/2013 | Dohrmann | |
| 8,374,171 B2 | 2/2013 | Cho et al. | |
| 8,377,360 B2* | 2/2013 | Nye | B41J 3/4073 |
| | | | 425/375 |
| 8,392,344 B2* | 3/2013 | Bartholomay | G06Q 30/0251 |
| | | | 706/12 |
| 8,400,491 B1 | 3/2013 | Panpaliya et al. | |
| 8,401,275 B2 | 3/2013 | Wang et al. | |
| 8,423,284 B2 | 4/2013 | O'Shea | |
| 8,451,731 B1 | 5/2013 | Lee et al. | |
| 8,463,435 B2 | 6/2013 | Herzog et al. | |
| 8,478,901 B1* | 7/2013 | Poursohi | H04L 67/10 |
| | | | 901/1 |
| 8,503,340 B1 | 8/2013 | Xu | |
| 8,515,577 B2 | 8/2013 | Wang et al. | |
| 8,527,094 B2 | 9/2013 | Kumar et al. | |
| 8,532,860 B2 | 9/2013 | Daly | |
| 8,554,307 B2* | 10/2013 | Razzaque | A61B 8/483 |
| | | | 600/407 |
| 8,610,786 B2 | 12/2013 | Ortiz | |
| 8,612,051 B2 | 12/2013 | Norman et al. | |
| 8,639,644 B1* | 1/2014 | Hickman | G06N 3/008 |
| | | | 706/14 |
| 8,639,797 B1 | 1/2014 | Pan et al. | |
| 8,670,017 B2 | 3/2014 | Stuart et al. | |
| 8,670,816 B2* | 3/2014 | Green | A61B 5/0066 |
| | | | 600/424 |
| 8,726,454 B2 | 5/2014 | Gilbert, Jr. et al. | |
| 8,754,925 B2 | 6/2014 | Ng et al. | |
| 8,836,751 B2 | 9/2014 | Ballantyne et al. | |
| 8,849,679 B2 | 9/2014 | Wang et al. | |
| 8,849,680 B2 | 9/2014 | Wright et al. | |
| 8,861,750 B2 | 10/2014 | Roe et al. | |
| 8,874,266 B1* | 10/2014 | Francis, Jr. | B25J 9/161 |
| | | | 700/250 |
| 8,897,920 B2 | 11/2014 | Wang et al. | |

(56) References Cited

U.S. PATENT DOCUMENTS

| | | | |
|---|---|---|---|
| 8,902,278 B2 | 12/2014 | Pinter et al. | |
| 8,918,209 B2 * | 12/2014 | Rosenstein | G06T 7/521 |
| | | | 700/250 |
| 8,918,213 B2 * | 12/2014 | Rosenstein | B25J 5/007 |
| | | | 700/258 |
| 8,930,019 B2 * | 1/2015 | Allen | G06F 1/1632 |
| | | | 700/250 |
| 8,935,005 B2 * | 1/2015 | Rosenstein | G05D 1/0274 |
| | | | 700/259 |
| 8,965,578 B2 | 2/2015 | Versteeg et al. | |
| 9,008,839 B1 * | 4/2015 | Kuffner, Jr. | G06Q 10/06 |
| | | | 700/248 |
| 9,024,771 B1 * | 5/2015 | Kuffner, Jr. | B25J 9/0084 |
| | | | 340/679 |
| 9,282,947 B2 * | 3/2016 | Razzaque | A61B 8/0841 |
| 9,296,109 B2 | 3/2016 | Cross et al. | |
| 9,436,993 B1 * | 9/2016 | Stolka | G06T 7/11 |
| 9,518,821 B2 * | 12/2016 | Malay | G01C 9/005 |
| 9,586,471 B2 * | 3/2017 | Gillett | G05D 1/0016 |
| 9,679,199 B2 * | 6/2017 | Wilson | G06F 3/0346 |
| 10,067,504 B1 * | 9/2018 | Qu | B64C 39/024 |
| 10,524,787 B2 * | 1/2020 | Shelton, IV | A61B 17/068 |
| 10,539,787 B2 * | 1/2020 | Haddick | G06F 3/0428 |
| 10,625,593 B2 * | 4/2020 | Gillett | B62K 25/02 |
| 10,685,481 B2 * | 6/2020 | Tran | A61B 5/0205 |
| 2001/0002448 A1 | 5/2001 | Wilson et al. | |
| 2001/0010053 A1 | 7/2001 | Ben-Shachar et al. | |
| 2001/0020200 A1 | 9/2001 | Das et al. | |
| 2001/0034475 A1 | 10/2001 | Flach et al. | |
| 2001/0034544 A1 | 10/2001 | Mo | |
| 2001/0037163 A1 | 11/2001 | Allard | |
| 2001/0048464 A1 | 12/2001 | Barnett | |
| 2001/0051881 A1 | 12/2001 | Filler | |
| 2001/0054071 A1 | 12/2001 | Loeb | |
| 2001/0055373 A1 | 12/2001 | Yamashita | |
| 2002/0015296 A1 | 2/2002 | Howell et al. | |
| 2002/0027597 A1 | 3/2002 | Sachau | |
| 2002/0027652 A1 | 3/2002 | Paromtchik et al. | |
| 2002/0033880 A1 | 3/2002 | Sul et al. | |
| 2002/0038168 A1 | 3/2002 | Kasuga et al. | |
| 2002/0044201 A1 | 4/2002 | Alexander et al. | |
| 2002/0049517 A1 | 4/2002 | Ruffner | |
| 2002/0055917 A1 | 5/2002 | Muraca | |
| 2002/0057279 A1 | 5/2002 | Jouppi | |
| 2002/0058929 A1 | 5/2002 | Green | |
| 2002/0059587 A1 | 5/2002 | Cofano et al. | |
| 2002/0063726 A1 | 5/2002 | Jouppi | |
| 2002/0073429 A1 | 6/2002 | Beane et al. | |
| 2002/0082498 A1 | 6/2002 | Wendt et al. | |
| 2002/0085030 A1 | 7/2002 | Ghani | |
| 2002/0095238 A1 | 7/2002 | Ahlin et al. | |
| 2002/0095239 A1 | 7/2002 | Wallach et al. | |
| 2002/0098879 A1 | 7/2002 | Rheey | |
| 2002/0104094 A1 | 8/2002 | Alexander et al. | |
| 2002/0106998 A1 | 8/2002 | Presley et al. | |
| 2002/0109770 A1 | 8/2002 | Terada | |
| 2002/0109775 A1 | 8/2002 | White et al. | |
| 2002/0111988 A1 | 8/2002 | Sato | |
| 2002/0120362 A1 | 8/2002 | Lathan et al. | |
| 2002/0128985 A1 | 9/2002 | Greenwald | |
| 2002/0130950 A1 | 9/2002 | James et al. | |
| 2002/0133062 A1 | 9/2002 | Ayling et al. | |
| 2002/0141595 A1 | 10/2002 | Jouppi | |
| 2002/0143923 A1 | 10/2002 | Alexander | |
| 2002/0177925 A1 | 11/2002 | Onishi et al. | |
| 2002/0183894 A1 | 12/2002 | Wang et al. | |
| 2002/0184674 A1 | 12/2002 | Xi et al. | |
| 2002/0186243 A1 | 12/2002 | Ellis et al. | |
| 2003/0021107 A1 | 1/2003 | Howell et al. | |
| 2003/0030397 A1 | 2/2003 | Simmons | |
| 2003/0048481 A1 | 3/2003 | Kobayashi et al. | |
| 2003/0050733 A1 | 3/2003 | Wang et al. | |
| 2003/0050734 A1 | 3/2003 | Lapham | |
| 2003/0060808 A1 | 3/2003 | Wilk | |
| 2003/0063600 A1 | 4/2003 | Noma et al. | |
| 2003/0069752 A1 | 4/2003 | Ledain et al. | |
| 2003/0080901 A1 | 5/2003 | Piotrowski | |
| 2003/0100892 A1 | 5/2003 | Morley et al. | |
| 2003/0104806 A1 | 6/2003 | Ruef et al. | |
| 2003/0112823 A1 | 6/2003 | Collins et al. | |
| 2003/0114962 A1 | 6/2003 | Niemeyer et al. | |
| 2003/0120714 A1 | 6/2003 | Wolff et al. | |
| 2003/0126361 A1 | 7/2003 | Slater et al. | |
| 2003/0135097 A1 | 7/2003 | Wiederhold et al. | |
| 2003/0135203 A1 | 7/2003 | Wang et al. | |
| 2003/0144579 A1 | 7/2003 | Buss | |
| 2003/0144649 A1 | 7/2003 | Ghodoussi et al. | |
| 2003/0151658 A1 | 8/2003 | Smith | |
| 2003/0152145 A1 | 8/2003 | Kawakita | |
| 2003/0171710 A1 | 9/2003 | Bassuk et al. | |
| 2003/0174285 A1 | 9/2003 | Trumbull | |
| 2003/0180697 A1 | 9/2003 | Kim et al. | |
| 2003/0195662 A1 | 10/2003 | Wang et al. | |
| 2003/0199000 A1 | 10/2003 | Valkirs et al. | |
| 2003/0206242 A1 | 11/2003 | Choi | |
| 2003/0212472 A1 | 11/2003 | McKee | |
| 2003/0216833 A1 | 11/2003 | Mukai et al. | |
| 2003/0216834 A1 | 11/2003 | Allard | |
| 2003/0220541 A1 | 11/2003 | Salisbury, Jr. et al. | |
| 2003/0220715 A1 | 11/2003 | Kneifel, II et al. | |
| 2003/0231244 A1 | 12/2003 | Bonilla et al. | |
| 2003/0232649 A1 | 12/2003 | Gizis et al. | |
| 2003/0236590 A1 | 12/2003 | Park et al. | |
| 2004/0001197 A1 | 1/2004 | Ko et al. | |
| 2004/0001676 A1 | 1/2004 | Colgan et al. | |
| 2004/0008138 A1 | 1/2004 | Hockley, Jr. et al. | |
| 2004/0010344 A1 | 1/2004 | Hiratsuka et al. | |
| 2004/0012362 A1 | 1/2004 | Tsurumi | |
| 2004/0013295 A1 | 1/2004 | Sabe et al. | |
| 2004/0017475 A1 | 1/2004 | Akers et al. | |
| 2004/0019406 A1 | 1/2004 | Wang et al. | |
| 2004/0024490 A1 | 2/2004 | McLurkin et al. | |
| 2004/0041904 A1 | 3/2004 | Lapalme et al. | |
| 2004/0065073 A1 | 4/2004 | Nash | |
| 2004/0068657 A1 | 4/2004 | Alexander et al. | |
| 2004/0078219 A1 | 4/2004 | Kaylor et al. | |
| 2004/0080610 A1 | 4/2004 | James et al. | |
| 2004/0088077 A1 | 5/2004 | Jouppi et al. | |
| 2004/0088078 A1 | 5/2004 | Jouppi et al. | |
| 2004/0093409 A1 | 5/2004 | Thompson et al. | |
| 2004/0095516 A1 | 5/2004 | Rohlicek | |
| 2004/0098167 A1 | 5/2004 | Yi et al. | |
| 2004/0102167 A1 | 5/2004 | Shim et al. | |
| 2004/0107254 A1 | 6/2004 | Ludwig et al. | |
| 2004/0107255 A1 | 6/2004 | Ludwig et al. | |
| 2004/0117065 A1 | 6/2004 | Wang et al. | |
| 2004/0117067 A1 | 6/2004 | Jouppi | |
| 2004/0123158 A1 | 6/2004 | Roskind | |
| 2004/0135879 A1 | 7/2004 | Stacy et al. | |
| 2004/0138547 A1 | 7/2004 | Wang et al. | |
| 2004/0143421 A1 | 7/2004 | Wang et al. | |
| 2004/0148638 A1 | 7/2004 | Weisman et al. | |
| 2004/0150725 A1 | 8/2004 | Taguchi | |
| 2004/0153211 A1 | 8/2004 | Kamoto et al. | |
| 2004/0157612 A1 | 8/2004 | Kim | |
| 2004/0162637 A1 | 8/2004 | Wang et al. | |
| 2004/0167666 A1 | 8/2004 | Wang et al. | |
| 2004/0167668 A1 | 8/2004 | Wang et al. | |
| 2004/0168148 A1 | 8/2004 | Goncalves et al. | |
| 2004/0170300 A1 | 9/2004 | Jouppi | |
| 2004/0172301 A1 | 9/2004 | Mihai et al. | |
| 2004/0172306 A1 | 9/2004 | Wohl et al. | |
| 2004/0174129 A1 | 9/2004 | Wang et al. | |
| 2004/0175684 A1 | 9/2004 | Kaasa et al. | |
| 2004/0179714 A1 | 9/2004 | Jouppi | |
| 2004/0186623 A1 | 9/2004 | Dooley et al. | |
| 2004/0189700 A1 | 9/2004 | Mandavilli et al. | |
| 2004/0201602 A1 | 10/2004 | Mody et al. | |
| 2004/0205664 A1 | 10/2004 | Prendergast | |
| 2004/0215490 A1 | 10/2004 | Duchon et al. | |
| 2004/0218099 A1 | 11/2004 | Washington | |
| 2004/0222638 A1 | 11/2004 | Bednyak | |
| 2004/0224676 A1 | 11/2004 | Iseki | |

(56) References Cited

U.S. PATENT DOCUMENTS

| | | |
|---|---|---|
| 2004/0230340 A1 | 11/2004 | Fukuchi et al. |
| 2004/0240981 A1 | 12/2004 | Dothan et al. |
| 2004/0241981 A1 | 12/2004 | Doris et al. |
| 2004/0260790 A1 | 12/2004 | Balloni et al. |
| 2005/0001582 A1 | 1/2005 | Goto et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castle et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182295 A1* | 8/2005 | Soper ............ A61B 1/0008 600/117 |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0264649 A1 | 12/2005 | Chang et al. |
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek, Jr. et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0064092 A1 | 3/2007 | Sandberg et al. |
| 2007/0078566 A1 | 4/2007 | Wang et al. |
| 2007/0093279 A1 | 4/2007 | Janik |
| 2007/0112700 A1 | 5/2007 | Den et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0167702 A1 | 7/2007 | Hasser et al. |
| 2007/0170886 A1 | 7/2007 | Plishner |
| 2007/0176060 A1 | 8/2007 | White et al. |
| 2007/0192910 A1* | 8/2007 | Vu ............ B25J 19/06 901/17 |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'Andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |

(56) References Cited

U.S. PATENT DOCUMENTS

| | | |
|---|---|---|
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0263628 A1 | 10/2008 | Norman et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0237317 A1 | 9/2009 | Rofougaran |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0228249 A1 | 9/2010 | Mohr et al. |
| 2010/0250497 A1 | 9/2010 | Redlich et al. |
| 2010/0268383 A1 | 10/2010 | Wang et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0130636 A1* | 6/2011 | Daniel .................. B64C 39/024 709/201 |
| 2011/0153198 A1 | 6/2011 | Kokkas et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0215674 A1 | 9/2011 | Rinner et al. |
| 2011/0245973 A1 | 10/2011 | Wang et al. |
| 2011/0280551 A1 | 11/2011 | Sammon |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092154 A1 | 4/2012 | Tran |
| 2012/0095352 A1 | 4/2012 | Tran |
| 2012/0113856 A1 | 5/2012 | Krishnaswamy |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0253200 A1* | 10/2012 | Stolka .................. A61B 90/13 600/459 |
| 2012/0291809 A1 | 11/2012 | Kuhe et al. |
| 2013/0016185 A1* | 1/2013 | Stolka .................. A61B 90/13 348/E5.025 |
| 2013/0216114 A1* | 8/2013 | Courtney .................. A61B 6/03 382/128 |
| 2013/0218024 A1* | 8/2013 | Boctor .................. A61B 6/4441 600/476 |
| 2013/0250938 A1 | 9/2013 | Anandakumar et al. |
| 2013/0338914 A1* | 12/2013 | Weiss .................. G08G 1/0129 340/905 |
| 2014/0044325 A1* | 2/2014 | Ma .................. G06T 7/33 382/128 |
| 2014/0047022 A1 | 2/2014 | Chan et al. |
| 2014/0085543 A1 | 3/2014 | Hartley et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |
| 2015/0182191 A1* | 7/2015 | Caluser .................. A61B 5/061 600/407 |
| 2017/0289771 A1* | 10/2017 | Magid .................. G01C 21/206 |
| 2018/0250086 A1* | 9/2018 | Grubbs .................. A61B 34/35 |
| 2018/0338806 A1* | 11/2018 | Grubbs .................. A61B 34/30 |
| 2019/0167059 A1* | 6/2019 | Brown .................. A47L 9/2805 |
| 2019/0339693 A1* | 11/2019 | Menon .................. G05D 1/0061 |
| 2019/0365305 A1* | 12/2019 | Hamidian .................. A61B 5/16 |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 466492 A2 | 1/1992 |
| EP | 488673 A2 | 6/1992 |
| EP | 0981905 B1 | 1/2002 |
| EP | 1262142 A2 | 12/2002 |
| EP | 1304872 A1 | 4/2003 |
| EP | 1536660 A2 | 6/2005 |
| EP | 1573406 A2 | 9/2005 |
| EP | 1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1536660 A3 | 4/2008 |
| EP | 1928310 A2 | 6/2008 |

(56) References Cited

FOREIGN PATENT DOCUMENTS

| | | |
|---|---|---|
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 A2 | 12/2010 |
| EP | 2300930 A1 | 3/2011 |
| EP | 2342651 A1 | 7/2011 |
| GB | 2431261 A | 4/2007 |
| JP | 7-194609 A | 8/1995 |
| JP | 7-213753 A | 8/1995 |
| JP | 7-248823 A | 9/1995 |
| JP | 7-257422 A | 10/1995 |
| JP | 884328 A | 3/1996 |
| JP | 8320727 A | 12/1996 |
| JP | 9-267276 A | 10/1997 |
| JP | 1079097 A | 3/1998 |
| JP | 10288689 A | 10/1998 |
| JP | 11220706 A | 8/1999 |
| JP | 2000-032319 A | 1/2000 |
| JP | 2000-049800 A | 2/2000 |
| JP | 2000-079587 A | 3/2000 |
| JP | 2000-188124 A | 7/2000 |
| JP | 2000-196876 A | 7/2000 |
| JP | 2000-235423 A | 8/2000 |
| JP | 2001-088124 A | 4/2001 |
| JP | 2001-125641 A | 5/2001 |
| JP | 2001-147718 A | 5/2001 |
| JP | 2001-179663 A | 7/2001 |
| JP | 2001-198865 A | 7/2001 |
| JP | 2001-198868 A | 7/2001 |
| JP | 2001-199356 A | 7/2001 |
| JP | 2002-000574 A | 1/2002 |
| JP | 2002-046088 A | 2/2002 |
| JP | 2002-101333 A | 4/2002 |
| JP | 2002-112970 A | 4/2002 |
| JP | 2002-235423 A | 8/2002 |
| JP | 2002-305743 A | 10/2002 |
| JP | 2002-321180 A | 11/2002 |
| JP | 2002-355779 A | 12/2002 |
| JP | 2004-181229 A | 7/2004 |
| JP | 2004-524824 A | 8/2004 |
| JP | 2004-261941 A | 9/2004 |
| JP | 2004-289379 A | 10/2004 |
| JP | 2005-028066 A | 2/2005 |
| JP | 2005-059170 A | 3/2005 |
| JP | 2005-111083 A | 4/2005 |
| JP | 2006-508806 A | 3/2006 |
| JP | 2006-109094 A | 4/2006 |
| JP | 2006-224294 A | 8/2006 |
| JP | 2006-246438 A | 9/2006 |
| JP | 2007-007040 A | 1/2007 |
| JP | 2007-081646 A | 3/2007 |
| JP | 2007-232208 A | 9/2007 |
| JP | 2007-316966 A | 12/2007 |
| JP | 2009-125133 A | 6/2009 |
| JP | 2010-064154 A | 3/2010 |
| JP | 2010-532109 A | 9/2010 |
| JP | 2010-246954 A | 11/2010 |
| KR | 10-2006-0037979 A | 5/2006 |
| KR | 10-2009-0012542 A | 2/2009 |
| KR | 10-2010-0019479 A | 2/2010 |
| KR | 10-2010-0139037 A | 12/2010 |
| WO | 93/006690 A1 | 4/1993 |
| WO | 97/042761 A1 | 11/1997 |
| WO | 1998/51078 A1 | 11/1998 |
| WO | 99/067067 A1 | 12/1999 |
| WO | 2000/25516 A1 | 5/2000 |
| WO | 2000/033726 A1 | 6/2000 |
| WO | 01/31861 A1 | 5/2001 |
| WO | 2003/077745 A1 | 9/2003 |
| WO | 2004/008738 A1 | 1/2004 |
| WO | 2004/012018 A2 | 2/2004 |
| WO | 2004/075456 A2 | 9/2004 |
| WO | 2006/012797 A1 | 2/2006 |
| WO | 2006/044847 A2 | 4/2006 |
| WO | 2006/078611 A3 | 7/2006 |
| WO | 2007/041295 A2 | 4/2007 |
| WO | 2007/041038 A3 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 4/2010 |
| WO | 2010/062798 A1 | 6/2010 |
| WO | 2010/065257 A1 | 6/2010 |
| WO | 2010/120407 A1 | 10/2010 |
| WO | 2011/028589 A2 | 3/2011 |
| WO | 2011/028589 A3 | 4/2011 |
| WO | 2011/097130 A2 | 8/2011 |
| WO | 2011/097132 A2 | 8/2011 |
| WO | 2011/109336 A2 | 9/2011 |
| WO | 201/149902 A2 | 12/2011 |
| WO | 2011/097132 A3 | 12/2011 |
| WO | 2011/149902 A3 | 12/2011 |

OTHER PUBLICATIONS

Hannes Bergkvist, Quadcopter Control using Android-based Sensing, University of Lund, MSc Thesis, No. ISRN LUTFD2/TFRT-5936—SE—ISSN 0280-5316 (2013).*

Tipsuwan et al., "Gain Adaptation of Networked Movile Robot to Compensate QoS Deterioration", vol. 4, 28th Annual Conference of the Industrial Electronics Society, Nov. 5-8, 2002, pp. 3146-2151.

"Appeal from the U.S. District Court for the Central District of California in No. 11-CV-9185, Judge Percy Anderson", May 9, 2014, pp. 1-46.

"Defendant VGo Communications, Inc.'s Invalidity Contentions Pursuant to the Feb. 27, 2012 Civil Minute Order", U.S. District Court for the Central District of California, in Case No. CV11-9185 PA, May 2, 2012, 143 pages.

"Google translation of: Innovations Report", From research project to television star: Care-O-bot in ZDF series, available online at <http://www.innovations-report.de/specials/printa.php?id=5157>, Sep. 28, 2001.

"Magne Charge", Smart Power for Electric Vehicles, General Motors Corporation, Serial No. 75189637, Registration No. 2114006, Filing Date: Oct. 29, 1996, Aug. 26, 1997, 2 pages.

"More Online Robots: Robots that Manipulate", available online at <http://ford.ieor.berkeley.edu/ir/robots.sub.-a2.html>. retrieved on Nov. 23, 2010, Aug. 2001, 2 pages.

"MPEG File Format Summary", downloaded from: <http://www.fileformat.info/format/mpeg/egff.htm>, Feb. 1, 2001, 8 pages.

"MPEG-4: a Powerful Standard for Use in Web and Television Environments", by Rob Koenen (KPN Research), downloaded from <http://www.w3.org/Architecture/1998/06/Workshop/paper26>, Jul. 1, 1998, 4 pages.

"Nomad XR4000 Hardware Manual", Release 1.0, Nomadic Technologies, Inc., Mar. 1999, 34 pages.

"PictureTel Adds New Features and Functionality to its Award-Winning Live200 Desktop Videoconferencing System", PR Newswire Association, LLC, Gale, Cengage Learning, Jun. 13, 1997, 4 pages.

"Robart I, II, III", Spawar, Systems Center Pacific, Available online at <http://www.nosc.mil/robots/land/robart/robart.html>, retrieved on Nov. 22, 2010, 1998, 8 pages.

"Using your Infrared Cell Phone Camera", Available on <http://www.catsdomain.com/xray/about.htm>, retrieved on Jan. 23, 2014, Courtesy of Internet Wayback Machine, Jan. 30, 2010, 4 pages.

ACM Digital Library Record, Autonomous Robots, vol. 11, No. 1, Table of Content, available at <http://dl.acm.org/citation.cfm?id=591550&picked=prox&cfid=360891374&c-ftoken=35225929>, Jul. 2001, 2 pages.

Active Media, Inc. "Saphira Software Manual", Real World, Saphira Version 5.3, 1997, 105 pages.

Activmedia Robotics LLC, "Pioneer 2/PeopleBot.TM.", Operations Manual, Version 9, Oct. 2001, 78 pages.

(56) References Cited

OTHER PUBLICATIONS

Adams, Chris, "Simulation of Adaptive Behavior (SAB'02)—From Animals to Animats 7", Mobile Robotics Research Group, The Seventh International Conference, available online at <http://www.dai.ed.ac.uk/groups/mrg/MRG.html>, retrieved on Jan. 22, 2014, Aug. 4-11, 2002, 1 pages.

Ando et al., "A Multimedia Self-Service Terminal with Conferencing Functions", Proceedings of 4th IEEE International Workshop on Robot and Human Communication, RO-MAN'95, Jul. 5-7, 1995, pp. 357-362.

Android Amusement Corp., "Renting Robots from Android Amusement Corp!", What Marketing Secret, (Advertisement), 1982, 1 page.

Appeal from the U.S. District Court for the Central District of California in case No. 11-cv-9185, Judge Percy Anderson, Joint Appendix, vol. I of IV, Jun. 24, 2013, pp. A1-A6357.

Appeal from the U.S. District Court for the Central District of California in case No. 11-cv-9185, Judge Percy Anderson, Joint Appendix, vol. II of IV, Jun. 24, 2013, pp A6849-A10634.

Appeal from the U.S. District Court for the Central District of California in case No. 11-cv-9185, Judge Percy Anderson, Joint Appendix, vol. III of IV, Jun. 24, 2013, pp. A10654-A15517.

Appeal from the U.S. District Court for the Central District of California in case No. 11-cv-9185, Judge Percy Anderson, Joint Appendix, vol. IV of IV, Jun. 24, 2013, pp. A15677-A18127.

Apple Inc. "I Phone", iPhone Series, XP002696350, Sep. 21, 2012, pp. 1-29.

Applebome, "Planning Domesticated Robots for Tomorrow's Household", New York Times, available online at <http://www.theoldrobots.com/images17/dc17.JPG>, Mar. 4, 1982, 1 page.

Bar-Cohen et al., "Virtual Reality Robotic Telesurgery Simulations Using MEMICA Haptic System", Proceedings of SPIE's 8th Annual International Symposium on Smart Structures and Materials, Mar. 5-8, 2001, 8 pages.

Barrett, Rick, "Video Conferencing Business Soars as Companies Cut Travel; Some Travel Cuts are Permanent", available online at <http//www.ivci.com/international.sub.-videoconferencing.sub.--news-sub.--videoconferencing.sub-news.sub-19.html>, May 13, 2002, 2 pages.

Bartholomew, "Pharmacy Apothecary of England", BnF-Teaching Kit—Childhood in the Middle Ages, available online al <http://classes.bnf.fr/ema/grands/034.htm>, retrieved on Jul. 26, 2012, 2 pages.

Bauer et al., "Remote Telesurgical Mentoring: Feasibility and Efficacy", IEEE, Proceedings of the 33rd Hawaii International Conference on System Sciences, 2000, pp. 1-9.

Bauer, Jeffrey C., "Service Robots in Health Care: The Evolution of Mechanical Solutions to Human Resource Problems", BonSecours Health System, Inc., Technology Ealy Warning System, Jun. 2003, pp. 1-10.

Bischoff, Rainer, "Design Concept and Realization of the Humanoid Service Robot HERMES", In A. Zelinsky (ed.) Field and Service Robotics, Springer, London, 1998, pp. 485-492.

Blackwell, Gerry, "Video: A Wireless LAN Killer App?", Availabel online at <http://www.wi-fiplanet.com/columns/article.php/1010261/Video-A-Wirele-ss-LAN-Killer>, retrieved on Nov. 22, 2010, Apr. 16, 2002, 4 pages.

Blaer et al., "TopBot: Automated Network Topology Detection With a Mobile Robot", IEEE, Proceedings of the 2003 International Conference on Robotics and Automation, Taipei, Taiwan, Sep. 14-19, 2003, pp. 1582-1587.

Bradner, S., "The Internet Standards Process-Revision 3", Network Working Group, Request for Comments: 2026, BCP: 9, Obsoletes: 1602, Category: Best Current Practice, Oct. 1996, pp. 1-36.

Brenner, Pablo, "A Technical Tutorial on the IEEE 802.11 Protocol", BreezeCOM Wireless Communications, Jul. 18, 1996, pp. 1-24.

Breslow et al., "Effect of a Multiple-Site Intensive Care Unit Telemedicine Program on Clinical and Economic Outcome an Alternative Paradigm for Intensivist Staffing", Critical Care Med., vol. 32, No. 1, Jan. 2004, pp. 31-38.

Brooks, Rodney A., "A Robust Layered Control System fora Mobile Robot", IEEE, Journal of Robotics and Automation, vol. 2, No. 1, Mar. 1986, pp. 14-23.

Brooks, Rodney Allen, "Flesh and Machines: How Robots Will Change US", available online at <http://dl.acm.org/citation.cfm?id-560264&preflayoul-nat%25202%2520of->, retrieved on Nov. 23, 2010, Feb. 2002, 3 pages.

Celi et al., "The eICU: It's Not Just Telemedicine", Critical Care Medicine, vol. 29, No. 8 (Supplement), Aug. 2001, pp. 183-189.

Cheetham et al., "Interface Development for a Child's Video Conferencing Robot", Centre for Learning Technologies, Ryerson University, 2000, 4 pages.

Christensen et al., "BeeSoft User's Guide and Reference", Robots for the Real World.TM., Real World Interface, Inc., Sep. 26, 1997, 203 pages.

Chu et al., "Detection of Target Mobile Signal Strength", Technical Development, Motorola Inc., Jan. 1999, pp. 205-206.

Civil Minutes-General: Case No. Cv 11-9185PA (AJWx), InTouch Tech., Inc. v. VGo Commons, Inc., U.S. District Court for the Central District of California, Judge Percy Anderson, Sep. 10, 2012, 7 pages.

Cleary et al., "State of the Art in Surgical Robotics: Clinical Applications and Technology Challenges", Computer Aided Surgery, Nov. 2001, pp. 1-26.

CMU Course 16×62, "Robot user's manual", (describing the Nomad Scout), Carnegie Mellon University, Feb. 1, 2001, 11 pages.

CNN, "Floating 'Droids' to Roam Space Corridors of the Future", available online at <http://edition.cnn.com/2000/TECH/space/01/12/psa/> retrieved on Nov. 11, 2010., Jan. 12, 2000, 3 pages.

CNN.com, "Paging Dr.Robot: Machine Helps Doctors with Patients", available online at <http://edition.cnn.com/2003/TECH/ptech/09/29/doctor.robot.a- p/index.html>, retrieved on Sep. 30, 2003, 3 pages.

Crowley, Susan L., "Hello to Our Future", AARP Bulletin, available online at <http://www.cs.cmu.ed/-nursebot/web/press/aarp.99.sub.-14/millennium.html>, Jan. 2000, retrieved on Nov. 23, 2010, 12 pages.

Dalton, Barnaby, "Techniques for Web Telerobotics", Ph. D Thesis for degree of Doctor of Philosophy, University of Western Australia, available online at <http://telerobot.mech.uwa.edu.au/information.html>, 2001, 243 pages.

Dario et al., "A Robot Workstation for Diagnosis and Physical Therapy", IEEE Catalog No. 88TH0234-5, Centro "E. Piaggio" University of Pisa, Italy, 1989, pp. 67-72.

Davies, Brian, "Robotics in Minimally Invasive Surgery", Mechatronics in Medicine Lab, Dept. Mechanical Engineering, Imperial College, London SW7 2BX, The Institution of Electrical Engineers, IEE, Savoy Place, London WC2R OBL, UK, 1995, pp. 1-2.

Yamauchi, Brian, "PackBot: A Versatile Platform for Military Robotics", Proceedings of SPIE for Military Robotics, 2004, pp. 228-237.

Yong et al., "Robot Task Execution with Telepresence Using Virtual Reality Technology", International Conference on Mechatronic Technology, Nov. 30-Dec. 2, 1998, pp. 1-8.

International Preliminary Report on Patentability for Int'l Application No. PCT/US2011/37689 dated Dec. 6, 2012, 9 pages.

International Search Report and Written Opinion received for Int'l Application No. PCT/US11/37689 dated Dec. 23, 2011, 11 pages.

Roy, et al., "Towards Personal Service Robots for the Elderly", Internet, Mar. 7, 2002, 7 pgs.

Jouppi et al., "BiReality: Mutually-lmmersive Telepresence", Multimedia '04, Proceedings of the 12th Annual ACM International Conference on Multimedia, Oct. 10-16, 2004, pp. 860-867.

Jouppi et al., "First Steps Towards Mutually-lmmersive Mobile Telepresence", CSCW '02, Proceedings of the ACM conference on Computer Supported Cooperative Work, Nov. 16-20, 2002, pp. 354-363.

Kanehira et al., "Virtual Humanoid Robot Platform to Develop Controllers of Real Humanoid Robots without Porting", Proceedings of IEEE/RSJ International Conference on Intelligent Robots and Systems, vol. 2, Oct. 29-Nov. 3, 2001, pp. 1093-1099.

(56) References Cited

OTHER PUBLICATIONS

Kaplan et al., "An Internet Accessible Telepresence", Multimedia Systems Journal, vol. 5, 1996, 7 pages.
Keller et al., "An Interface for Raven", The National Aviary's Teleconferencing Robot, Interaction and Visual Interface Design, School of Design, Carnegie Mellon University, 2001, 8 pages.
Khatib et al., "Robots in Human Environments", Robotics Laboratory, Department of Computer Science, Stanford University, 1999, 15 pages.
Knight et al., "Active Visual Alignment of a Mobile Stereo Camera Platform", Robotics and Automation, Proceedings of ICRA '00, IEEE International Conference, vol. 4, Apr. 24-28, 2000, pp. 3203-3208.
Kurlowicz et al., "The Mini Mental State Examination (MMSE)", The Hartford Institute for Geriatric Nursing, Journal of Psychiatric Research, No. 3, Jan. 1999, 2 pages.
Kuzuoka et al., "Can the GestureCam be a Surrogate?", Proceedings of the Fourth European Conference on Computer-Supported Cooperative Work, Sep. 10-14, 1995, pp. 181-196.
Lane, Earl, "Automated Aides", available online at <http://www.cs.cum.edu/nursebot/web/press/nd4380.htm>, Reterieved on Nov. 23, 2010, Oct. 17, 2000, 4 pages.
Lee et al., "A Novel Method of Surgical Instruction: International Telementoring", World Journal of Urology, vol. 16, No. 6, Dec. 1998, pp. 367-370.
Leifer et al., "VIPRR: A Virtually in Person Rehabilitation Robot", Proceedings of 1997 International Conference on Rehabilitation Robotics, Apr. 14-15, 1997,4 pages.
Lemaire, Edward, "Using Communication Technology to Enhance Rehabilitation Services", Terry Fox Mobile Clinic, The Rehabilitation Centre, Ottawa, Canada, Version 2.0, 1998-2001, 104 pages.
Library of Congress, "008-Fixed-Length Data Elements (NR)", MARC 21 Format for Classification Data, available at <http://www.loc.gov/marc/classification/cd008.html>, retrieved on Jul. 22, 2014, pp. 1-14.
Lim et al., "Control to Realize Human-Like Walking of a Biped Humanoid Robot", Systems, Man and Cybernetics, IEEE International Conference, vol. 5, 2000, pp. 3271-3276.
Linebarger et al., "Concurrency Control Mechanisms for Closely Coupled Collaboration in Multithreaded Virtual Environments", Department of Computer Science and Engineering; Lehigh University, vol. 13, 2004, 40 pages.
Long, William F., "Robot Navigation Technology", available online at <http://www.atp.nist.gov/eao/sp950-1/helpmate.htm>, retrieved on Nov. 23, 2010, Mar. 1999, 3 pages.
Luna, Nancy, "Robot a New Face on Geriatric Care", ocregister.com, Aug. 6, 2003, 3 pages.
Mack, Michael J., "Minimally Invasive and Robotic Surgery", The Journal of the American Medical Association, vol. 285, No. 5, Feb. 7, 2001, pp. 568-572.
Mair, G. M., "Telepresence—The Technology and its Economic and Social Implications", Technology and Society, Technology and Society at a Time of Sweeping Change, Proceedings of International Symposium, Jun. 20-21, 1997, pp. 118-124.
Martin, Anya, "Brighter Days Ahead", Assisted Living Today, vol. 9, Nov./Dec. 2002, pp. 19-22.
McCardle et al., "The Challenge of Utilizing New Technology in Design Education", Loughborough University, IDATER, 2000, pp. 122-127.
Meng et al., "E-Service Robot in Home Healthcare", Proceedings of the 2000 IEEE/RSJ, International Conference on Intelligent Robots and Systems, 2000, pp. 832-837.
Metz, Cade, "HP Labs", available online at <http://www.pcmag.com/article2/0,2817,1130820,00.asp>, Jul. 1, 2003, 4 pages.
Michaud, Anne, "Introducing 'Nursebot'", available online at <http://www.cs.cmu.edu/.about.nursebot/web/press/globe.sub.-3.sub.-0- 1/index.html>, retrieved on May 5, 2008, Sep. 11, 2001, 4 pages.
Microsoft Corporation, Inc., "Microsoft NetMeeting 3 Features", available online at <http://technet.microsoft.com/en-us/library/cc723477.aspx>-;, retrieved on Jun. 26, 2012, 2012, 6 pages.
Minsky, Marvin, "Telepresence", OMNI Magazine, Jun. 1980, 6 pages.
Montemerlo, Mike, "Telepresence: Experiments in Next Generation Internet", available Online at <http://www.ri.cmu.edu/creative/archives.htm>, retrieved on May 25, 2008, Oct. 20, 1998, 3 pages.
Murphy, Robin R., "Introduction to AI Robotics", A Bradford Book, The Massachusetts Institute of Technology Press, 2000, 487 pages.
Nakajima et al., "A Multimedia Teleteaching System using an Electronic Whiteboard for Two-Way Communication of Motion Videos and Chalkboards", Robot and Human Communication, Proceedings of 2nd IEEE International Workshop, 1993, pp. 436-441.
Nakazato et al., "Group-Based Interface for Content-Based Image Retrieval", Proceedings of the Working Conference on Advanced Visual Interfaces, 2002, pp. 187-194.
Nakazato et al., "Group-Oriented User Interface for Digital Image Management", Journal of Visual Languages and Computing, vol. 14, No. 4, Aug. 2003, pp. 45-46.
Nersc, "Berkeley Lab's RAGE Telepresence Robot Captures R&D100 Award", Available online at <https://www.nersc.gov/news-publications/news/nersc-center-news/2002/b- erkeley-lab-s-rage-telepresence-robot-captures-r-and-d100-award/>. Retrieved on Jan. 22, 2014, Jul. 2, 2002, 2 pages.
Zipperer, Lorri, "Robotic Dispensing System", ISMP Medication Safety Alert, vol. 4, No. 17, Aug. 25, 1999, pp. 1-2.
Nomadic Technologies, Inc., "Nomad Scout Language Reference Manual", Software Version: 2.7, Part No. DOC00002, Jul. 12, 1999, 47 pages.
Nomadic Technologies, Inc., "Nomad Scout User's Manual", Software Version 2.7, Part No. DOC00004, Jul. 12, 1999, pp. 1-59.
Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.
North, Michael, "Telemedicine: Sample Script and Specifications for a Demonstration of Simple Medical Diagnosis and Treatment Using Live Two-Way Video on a Computer Network", Greenstar Corporation, 1998, 5 pages.
Office Action received for Chinese Patent Application No. 200680044698.0 dated Nov. 4, 2010. (9 pages of Official Copy and 17 pages of English Translation).
Ogata et al., "Development of Emotional Communication Robot: WAMOEBA-2R-Experimental evaluation of the Emotional Communication between Robotsand Humans", Proceedings of the 2000 IEEE/RSJ International Conference on Intelligent Robots and Systems, vol. 1, 2000, pp. 175-180.
Ogata et al., "Emotional Communication Robot: WAMOEBA-2R-Emotion Model and Evaluation Experiments", Proceedings of the International Conference on Humanoid Robots, 2000, pp. 1-16.
Oh et al., "Autonomous Battery Recharging for Indoor Mobile Robots", Proceedings of Australian Conference on Robotics and Automation, 2000, pp. 1-6.
Ojha, Anand K., "An application of Virtual Reality in Rehabilitation", Proceedings of the 1994 IEEE Southeastcon Creative Technology Transfer, A Global Affair, Apr. 1994, pp. 4-6.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
Osborn et al., "Quality of Life Technology Center", QoLT Research Overview: A National Science Foundation Engineering Research Center, Carnegie Mellon University of Pittsburgh, 2 pages.
Panusopone et al., "Performance comparison of MPEG-4 and H.263+ for streaming video applications", Circuits Systems Signal Processing, vol. 20, No. 3, 2001, pp. 293-309.
Paulos et al., "A World Wide Web Telerobotic Remote Environment Browser", available online at <http://www.w3.org/Conferences/WWW4/Papers/326/>, retrieved on Nov. 23, 2010, 1995, 15 pages.
Paulos et al., "Designing Personal Tele-Embodiment", Proceedings of IEEE International Conference on Robotics and Automation, vol. 4, May 16-20, 1998, pp. 3173-3178.
Paulos et al., "Personal Tele-Embodiment", Chapter 9 in Goldberg et al., Ed., "Beyond Webcams", MIT Press, Jan. 4, 2002, pp. 155-167.

(56) References Cited

OTHER PUBLICATIONS

Paulos et al., "PRoP: Personal Roving Presence", ACM:CHI Proceedings of CHI, 1998, 8 pages.
Davis, Erik, "Telefriend, Meet iRobot, The Smartest Webcam on Wheels", Wired Magazine, Issue 8.09, available online at <http://www.wired.com/wired/archive/8.09/irobot.html?pg=1&topic=&topic-.sub.-set=>, retrieved on Jul. 7, 2012, Sep. 2000, 3 pages.
Dean et al., "1992 AAAI Robot Exhibition and Competition", Articles, AI Magazine, vol. 14, No. 1, 1993, 15 pages.
Defendant-Counterclaimant VGo Communications, Inc.'s Supplemental Invalidity Contentions Pursuant to the Feb. 27, 2012 Civil Minute Order, U.S. District Court for the Central District of California, Case No. CV11-9185 PA, May 14, 2012, 228 pages.
Digiorgio, James, "Is Your Emergency Department of the Leading Edge?", Chicago Hospital News, vol. 2, No. 12, Feb. 2005, 3 pages.
Dudenhoeffer et al., "Command and Control Architectures for Autonomous Micro- Robotic Forces", FY00 Project Report, Idaho National Engineering and Environmental Laboratory, Human Systems Engineering and Sciences Department, Idaho Falls, Apr. 2001, 43 pages.
Elhajj et al., "Real-Time Haptic Feedback in Internet-Based Telerobotic Operation", IEEE International Conference on Electro/Information Technology, Jun. 2000, 10 pages.
Elhajj et al., "Supermedia in Internet-Based Telerobotic Operations", Lecture Notes in Computer Science, vol. 2216, 2001, pp. 359-372.
Elhajj et al., "Synchronization and Control of Supermedia Transmission via the Internet", Proceedings of 2001 International Symposium on Intelligent Multimedia Video and Speech Processing, Hong Kong, May 2-4, 2001, pp. 320-323.
Ellison et al., "Telerounding and Patient Satisfaction after Surgery", American College of Surgeons, Elsevier, Inc., vol. 199, No. 4, Oct. 2004, pp. 523-530.
Evans et al., "HelpMate: The Trackless Robotic Courier", PYXIS, available online at <http://www.pyxis.com/>, 3 pages.
Feis et al., "Developing a Video-Mediated Communication System for Hospitalized Children", Telemedicine Journal, vol. 5, No. 2, 1999, 30 pages.
Fetterman, David M., "Videoconferencing Over the Internet", Qualitative Health Journal, vol. 7, No. 1, May 1966. pp. 154-163.
Fiorini et al., "Health Care Robotics: A Progress Report", IEEE International Conference on Robotics and Automation, vol. 2, Apr. 20-25, 1997, pp. 1271-1276.
Fong, Terrence, "Collaborative Control: A Robot-Centric Model for Vehicle Teleoperation", The Robotics Institute Carnegie Mellon University, Nov. 2001, 197 pages.
Fulbright et al., "SWAMI: An Autonomous Mobile Robot for Inspection of Nuclear Waste of Storage Facilities", Autonomous Robots, 2, 1995, pp. 225-235.
Gaidioz et al., "Synchronizing Network Probes to Avoid Measurement Intrusiveness with the Network Weather Service", High-Performance Distributed Computing, Proceedings of the Ninth International Symposium, 2000; pp. 147-154.
Garner et al., "The Application of Telepresence in Medicine", BT Technology Journal, vol. 15, No. 4, Oct. 1, 1997, pp. 181-187.
Ghiasi et al., "A Generic Web-based Teleoperations Architecture: Details and Experience", Proceedings of SPIE, Telemanipulator and Telepresence Technologies VI, vol. 3840, No. 234, Sep. 19, 1999, 14 pages.
Goldberg et al., "Collaborative Teleoperation via the Internet", IEEE International Conference on Robotics and Automation (ICRA), vol. 2, San Francisco, California, 2000, pp. 2019-2024.
Goldberg et al., "Desktop Teleoperation via the World Wide Web", Proceedings of IEEE International Conference on Robotics and Automation, vol. 1, May 21, 27, 1995, p. 654 659.
Goldenberg et al., "Telemedicine in Otolaryngology", American Journal of Otolaryngology, vol. 23, No. 1, Jan. 2002, pp. 35-43.
Goldman, Lea, "Machine Dreams", available online at <http://www.forbes.com/global/2002/0527/043.html>, retrieved on Nov. 23, 2010., May 27, 2002, 5 pages.

Gostai "Gostai Jazz: Robotic Telepresence", available online at <http://www.gostai.com>, 4 pages.
Gump, Michael D., "Robot Technology Improves VA Pharmacies", U.S. Medicine Informational Central, Jul. 2001, 3 pages.
Hameed et al. "A Review of Telemedicine", Journal of Telemedicine and Telecare, vol. 5, Supplement 1, 1999, pp. 103-106.
Picturetel Corporation, "Introducing PictureTel Live200 for Windows NT", 1997, 63 pages.
Han et al., "Construction of an Omnidirectional Mobile Robot Platform Based on Active Dual-Wheel Caster Mechanisms and Development of a Control Simulator", Journal of Intelligent and Robotic Systems, Kluwer Acedemic Publishers, vol. 29, Nov. 2000, pp. 257-275.
Handley et al., "SDP: Session Description Protocol", RFC 2327, available Online at <http://www.faqs.org/rfcs/rfc2327.html>, retrieved on Nov. 23, 2010, Apr. 1998, 22 pages.
Hanebeck et al., "ROMAN: A Mobile Robotic Assistant for Indoor Service Applications", Proceedings of the IEEE/RSJ International Conference on Intelligent Robots and Systems, vol. 2, 1997, pp. 518-525.
Harmo et al., "Moving Eye-Interactive Telepresence over Internet with a Ball Shaped Mobile Robot", Automation Technology Laboratory, Helsinki University of Technology, 2000, 6 pages.
Haule et al., "Control Scheme for Delayed Teleoperation Tasks", Communications, Computers and Signal Processing, Proceedings of IEEE Pacific Rim Conference, May 17-19, 1995, pp. 157-160.
Hees, William P., "Communications Design for a Remote Presence Robot", CSCI E-131B, Final Project, Jan. 14, 2002, 12 pages.
Herias et al., "Flexible Virtual and Remote Laboratory for Teaching Robotics", FORMATEX 2006, Proceedings of Advance in Control Education Madrid, Spain, Jun. 2006, pp. 1959-1963.
Holmberg et al., "Development of a Holonomic Mobile Robot for Mobile Manipulation Tasks", FSR'99 International Conference on Field and Service Robotics, Pittsburgh, PA, Aug. 1999, 6 pages.
International Preliminary Report on Patentability and Written Opinion Received for International Patent Application No. PCT/US/200714099, dated Dec. 16, 2008, 5 pages.
Zorn, Benjamin G. "Ubiquitous Telepresence", Department of Computer Science, University of Colorado, Mar. 18, 1996, 13 pages.
International Preliminary Report on Patentability and Written Opinion Received for International Patent Application No. PCT/US2006/037076, dated Apr. 1, 2008, 6 pages.
International Search Report and Written Opinion Received for International Application No. PCT/US2006/037076, dated May 11, 2007, 6 pages.
International Preliminary Report on Patentability and Written Opinion Received for International Patent Application No. PCT/US2005/037347, dated Apr. 17, 2006, 7 pages.
International Search Report Received for International Patent Application No. PCT/US2007/14099, dated Jul. 30, 2008, 1 page.
Ishiguro et al., "Integrating a Perceptual Information Infrastructure with Robotic Avatars: A Framework for TeleExistence", Intelligent Robots and Systems, Proceedings of 1999 IEEE/RSJ International Conference, vol. 2, 1999, pp. 1032-1038.
Ishihara et al., "Intelligent Microrobot DDS (Drug Delivery System) Measured and Controlled by Ultrasonics", Proceedings of IEEE/RSJ International Workshop on Intelligent Robots and Systems, vol. 2, Nov. 3-5, 1991, pp. 1145-1150.
ITU, "A Far End Camera Control Protocol for Videoconferences Using H.224", Transmission of Non-Telephone Signals, ITU-T, Telecommunication Standardization Sector of ITU, H.281, Nov. 1994, 12 pages.
ITU, "Call Completion Supplementary Services for H.323", ITU-T, Telecommunication Standardization Sector of ITU, H.450.9, Series H: Audiovisual and Multimedia Systems, Nov. 2000, 63 pages.
ITU, "Call Intrusion Supplementary Service for H.323", ITU-T, Telecommunication Standardization Sector of ITU, H.450.11, Series H: Audiovisual and Multimedia Systems, Mar. 2001, 59 pages.
ITU, "Packet-Based Multimedia Communications Systems", ITU-T, Telecommunication Standardization Sector of ITU, H.323, Series H: Audiovisual and Multimedia Systems, Feb. 1998, 128 pages.
Ivanova, Natali, "Internet Based Interface for Control of a Mobile Robot", First Degree Programme in Mathematics and Computer

(56) References Cited

OTHER PUBLICATIONS

Science, Master.cndot.s thesis, Department of Numerical Analysis and Computer Science, 2003, 59 pages.
Jacobs et al., "Applying Telemedicine to Outpatient Physical Therapy", AMIA, Annual Symposium Proceedings, 2002, 1 page.
Jenkins et al. "Telehealth Advancing Nursing Practice", Nursing Outlook, vol. 49, No. 2, Mar. 2001, pp. 100-105.
Johanson, Mathias, "Supporting Video-Mediated Communication over the Internet", Thesis for the degree of Doctor of Philosophy, Department of Computer Engineering, Chalmers University of Technology, Gothenburg, Sweden, 2003, 222 pages.
Paulos et al., "Social Tele-Embodiment: Understanding Presence", Autonomous Robots, vol. 11, No. 1, Kluwer Academic Publishers, Jul. 2001, pp. 87-95.
Paulos et al., "Ubiquitous Tele-Embodiment: Applications and Implications", International Journal of Human Computer Studies, vol. 46, No. 6, Jun. 1997, pp. 861-877.
Paulos et al., "Video of PRoP 2 at Richmond Field Station", www.prop.org, Printout of Home Page of Website and Two-page Transcript of the Audio Portion of said PRoP Video, May 2001, 2 pages.
Paulos, Eric J., "Personal Tele-Embodiment", Dissertation, Doctor of Philosophy in Computer Science in the Graduate Division of the University of California at Berkeley, 2001, 282 pages.
Paulos, Eric John, "Personal Tele-Embodiment", Introductory and Cover Pages from 2001 Dissertation Including Contents table, together with E-mails Relating thereto from UC Berkeley Libraries, as Shelved at UC Berkeley Engineering Library (Northern Regional Library Facility), May 8, 2002, 25 pages (including 4 pages of e-mails).
Paulos, Eric John, "Personal Tele-Embodiment", OskiCat Catalog Record, UCB Library Catalog, Results page and MARC Display, retrieved on Jun. 14, 2014, 3 Pages.
Zamrazil, Kristie, "Telemedicine in Texas: Public Policy Concerns", Focus Report, House Research Organization, Texas House of Representatives, No. 76-22, May 5, 2000, pp. 1-16.
Pin et al., "A New Family of Omnidirectional and Holonomic Wheeled Platforms for Mobile Robots", IEEE Transactions on Robotics and Automation, vol. 10, No. 4, Aug. 1994, pp. 480-489.
Piquepaille, Roland, "How New Technologies are Modifying Our Way of Life", Roland Piquepaille's Technology Trends This Blog and its RSS Feed Are Moving, Oct. 31, 2004, 2 pages.
Radvision, "Making Sense of Bandwidth the NetSense Way", Network Congestion in Unmanaged Networks Bandwidth Estimation and Adaptation Techniques, Radvision's Netsense Technology, 2010, 7 pages.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Reply Brief for Plaintiff-Appellant InTouch Technologies, Inc., Appeal from the U.S. District Court for the Central Districi of California in Case No. 11-cv-9185, Judge Percy Anderson, Jun. 14, 2013, 39 pages.
Reynolds et al., "Review of Robotic Telemedicine Utilization in Intensive Care Units (ICUs)", 11th Annual ATA Symposium, Tampa, Florida, 2011, 1 page.
Roach, Adam, "Automatic Call Back Service in SIP", Internet Engineering Task Force, Internet Draft, Category: Informational, Mar. 2000, 8 pages.
Rovetta et al., "A New Telerobotic Application: Remote Laparoscopic Surgery Using Satellites and Optical Fiber Networks for Data Exchange", International Journal of Robotics Research, vol. 15, No. 3, Jun. 1, 1996, pp. 267-279.
Roy et al., "Towards Personal Service Robots for the Elderly", Workshop on Interactive Robots and Entertainment (WIRE 2000), vol. 25, Apr. 30-May 1, 2000, 7 pages.

Sachs et al., "Virtual Visit.TM.: Improving Communication for Those Who Need it Most", Studies in Health Technology and Informatics, vol. 94, Medicine Meets Virtual Reality 11, 2003, pp. 302-308.
Salemi et al., "MILO: Personal Robot Platform", IEEE/RSJ International Conference on Intelligent Robots and Systems, Aug. 2005, pp. 4089-4094.
Sandt et al., "Perceptions for a Transport Robot in Public Environments", Proceedings of the IEEE/RSJ International Conference on Intelligent Robots and Systems, vol. 1, Sep. 7-11, 1997, pp. 360-365.
Sawyer, Robert J., "Inventing the Future: 2000 Years of Discovery", Available online at <http://www.sfwriter.com/pritf.htm>, retrieved on May 25, 2008, Jan. 2, 2000, 2 pages.
Schaeffer et al., "Care-O-Bot.TM.: The Concept of a System for Assisting Elderly or Disabled Persons in Home Environments", Proceedings of the 24th Annual Conference of the IEEE Industrial Electronics Society, vol. 4, 1998, pp. 2476-2481.
Schraft et al., "Care-O-botTM: The Concept of a System for Assisting Elderly or Disabled Persons in Home Environments", IEEE Proceedings of the 24th Annual Conference of the Industrial Electronics Society, IECON '98, Aug. 31-Sep. 4, 1998, pp. 2476-2481.
Schultz et al., "Web Interfaces for Mobile Robots in Public Places", IEEE Robotics and Automation Magazine, vol. 7, No. 1, Mar. 2000, pp. 48-56.
Screenshot Showing Google Date for Lemaire Telehealth Manual, Screenshot Retrieved on Dec. 18, 2014, 1 page.
Shimoga et al., "Touch and Force Reflection for Telepresence Surgery", Proceedings of the 16th Annual International Conference of the IEEE Engineering in Medicine and Biology Society, Nov. 1994, pp. 1049-1050.
Siegwart et al., "Interacting Mobile Robots on the Web", Proceedings of the IEEE International Conference on Robotics and Automation, May 1999, pp. 10-15.
Simmons et al., "Xavier: An Autonomous Mobile Robot on the Web", IEEE Robotics and Automation Magazine, 1999, pp. 43-48.
Stephenson, Gary, "Dr. Robot Tested at Hopkins", Johns Hopkins Medical institutions, available online at <http://www.hopkinsmedicine.org/press/2003/august/030805.htm>, Aug. 5, 2003, 2 pages.
Stoianovici et al., "Robotic Tools for Minimally Invasive Urologic Surgery", Complications of Urologic Laparoscopic Surgery: Recognition, Management and Prevention, Dec. 2002, 17 pages.
Suplee, Carl, "Mastering the Robot", available online at <http://www.cs.cmu.edu-nursebotlweb/press/wash/index.html>, retrieved on Nov. 23, 2010, Sep. 17, 2000, 5 pages.
Tahboub et al., "Dynamics Analysis and Control of a Holonomic Vehicle With Continously Variable Transmission", Journal of Dynamic Systems, Measurement and Control ASME, vol. 124, Mar. 2002, pp. 118-126.
Telepresence Research, Inc., "Telepresence Mobile Robot System", available online at <http://www.telepresence.com/telepresence-research/TELEROBOT-/>, retrieved on Nov. 23, 2010, Feb. 20, 1995, 3 pages.
Tendick et al., "Human-Machine Interfaces for Minimally Invasive Surgery", Proceedings of the 19th Annual International Conference of the IEEE Engineering in Medicine and Biology Society, vol. 6, Oct. 30-Nov. 2, 1997, pp. 2771-2776.
Theodosiou et al., "MuLVAT: A Video Annotation Tool Based on XML-Dictionaries and Shot Clustering", 19th International Conference, Artificial Neural Networks-ICANN, Sep. 14-17, 2009, pp. 913-922.
Thrun et al., "Probabilistic Algorithms and the Interactive Museum Tour-Guide Robot Minerva", Journal of Robotics Research, vol. 19, 2000, pp. 1-35.
Time, Lists, "Office Coworker Robot", Best Inventions of 2001, Available online at <http://content.time.com/time/specials/packages/article/0,28-804,1936165.sub.-1936255.sub.-1936640,00.html>, Nov. 19, 2001, 2 pages.
Zambroski, James, "CMU, Pitt Developing 'Nursebot'", available online at <http://www.cs.cmu.edu/.about.nursebot/web/press/tribunereview.html>- ;, retrieved on Jun. 26, 2012, Oct. 27, 2000, 3 pages.

(56) References Cited

OTHER PUBLICATIONS

Tsui et al., "Exploring Use Cases for Telepresence Robots", 6th ACM/IEEE International Conference on Human-Robot Interaction (HRI), Mar. 2011, 7 pages.

Tyrrell et al., "Teleconsultation in Psychology: The Use of Videolinks for Interviewing and Assessing Elderly Patients", British Geriatrics Society, Age and Ageing, vol. 30, No. 3, May 2001, pp. 191-195.

Tzafestas et al., "VR-based Teleoperation of a Mobile Robotic Assistant: Progress Report", Technical Report DEMO 2000/13, Institute of Informatics and Telecommunications, National Center for Scientific Research "Demokritos", Athens, Greece, Nov. 2000, pp. 1-23.

U.S. Appl. No. 10/783,760, filed Feb. 20, 2004, 48 pages.

UMASS Lowell Robotics Lab, "Robotics Lab @ UMASS Lowell", Department of Computer Science, Brochure, 2011, 2 pages.

Urquhart, Kim, "InTouch's Robotic Companion 'Beams Up' Healthcare Experts", Medical Device Daily, The Daily Medical Technology Newspaper, vol. 7, No. 39, Feb. 27, 2003, pp. 1-4.

Video Middleware Cookbook, "H.350 Directory Services for Multimedia", 4 pages.

Wang et al., "A Healthcare Tele-robotic System with a Master Remote Station with an Arbitrator", U.S. Appl. No. 60/449,762, filed Feb. 24, 2003, 28 pages.

Weaver et al. "Monitoring and Controlling Using the Internet and Java", Proceedings of the 25th Annual Conference of the IEEE Industrial Electronics Society, vol. 3, 1999, pp. 1152-1158.

Weiss et al., "Telework and Video-Mediated Communication: Importance of Real-Time, Interactive Communication for Workers with Disabilities", Available online at <http://www.telbotics.com/research.sub.-3.htm>, retrieved on Nov. 23, 2010, 1999, 3 pages.

Weiss, et al., "PEBBLES: A Personal Technology for Meeting Education, Social and Emotional Needs of Hospitalised Children", Personal and Ubiquitous Computing, vol. 5, No. 3, Aug. 2001, pp. 157-168.

West et al., "Design of Ball Wheel Mechanisms for Omnidirectional Vehicles with Full Mobility and Invariant Kinematics", Journal of Mechanical Design, ASME, vol. 119, Jun. 1997, pp. 153-161.

Yamasaki et al., "Applying Personal Robots and Active Interface to Video Conference Systems", 6th International Conference on Human Computer Interaction, vol. B, 1995, pp. 243-248.

\* cited by examiner

TELEPRESENCE ROBOT SYSTEM THAT CAN BE ACCESSED BY A CELLULAR PHONE

CROSS-REFERENCE TO RELATED APPLICATIONS

This application is a continuation of application Ser. No. 12/785,791, filed May 24, 2010, now U.S. Pat. No. 10,343,283.

BACKGROUND OF THE INVENTION

1. Field of the Invention

The subject matter disclosed generally relates to the field of robotics.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

There has been marketed a mobile tele-presence robot introduced by InTouch Technologies, Inc., the assignee of this application, under the trademark RP-7. The InTouch robot is controlled by a user at a remote station. The remote station may include a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly. The remote stations of the InTouch systems are either laptop or personal computers. A user may not always have access to a computer. It would thus be desirable to allow access to a videoconferencing robot with other devices. This is particularly true when the user is in the medical field, such as a doctor, and time is of the essence.

BRIEF SUMMARY OF THE INVENTION

A robot system with a robot that has a camera, a monitor, a microphone and a speaker. The system also includes a cellular phone that can establish communication with the robot microphone and speaker.

DETAILED DESCRIPTION

Disclosed is a robot system with a robot that has a camera, a monitor, a microphone and a speaker. A communication link can be established with the robot through a cellular phone. The link may include an audio only communication. Alternatively, the link may include audio and video communication between the cellular phone and the robot. Because cellular phones typically have a lower resolution than devices such as computer monitors, the phone can transmit its resolution to the robot and cause the robot to transmit captured images at the phone resolution. The user can cause the robot to move through input on the cellular phone. For example, the phone may include an accelerometer that senses movement, and movement commands are then sent to the robot to cause a corresponding robot movement. The phone may have a touch screen that can be manipulated by the user to cause robot movement and/or camera zoom. The robot can also be accessed by different devices such as a laptop or a personal computer. Access by a laptop may include establishing both cellular and LAN links. Data such as video can be transmitted through the cellular link, while audio is sent through the LAN link.

Figure 1:
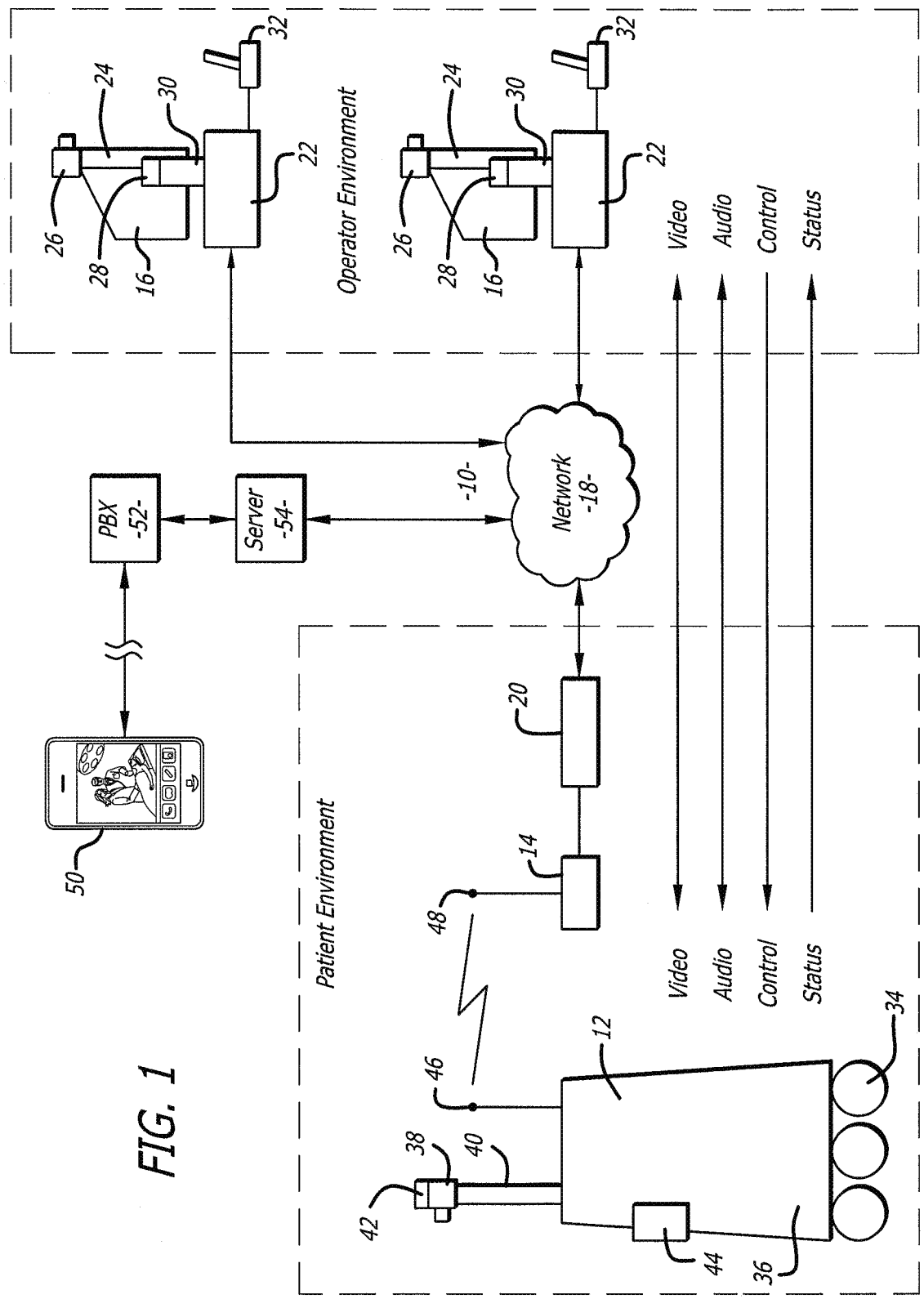
FIG. 1 is an illustration of a robotic system.

Referring to the drawings more particularly by reference numbers, FIG. 1 shows an embodiment of robot system 10. The robot system 10 includes a robot 12, a base station 14 and a plurality of remote control stations 16. Each remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device.

Each remote control station 16 may include a computer 22 that has a monitor 24, a camera 26, a microphone 28 and a speaker 30. The computer 22 may also contain an input device 32 such as a joystick or a mouse. Each control station 16 is typically located in a place that is remote from the robot 12. Although only one robot 12 is shown, it is to be understood that the system 10 may have a plurality of robots 12. In general any number of robots 12 may be controlled by any number of remote stations. For example, one remote station 16 may be coupled to a plurality of robots 12, or one robot 12 may be coupled to a plurality of remote stations 16. Likewise, one robot may be accessed through another robot.

The robot 12 includes a movement platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

Each remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The system 10 may allow a user to access the robot 12 through a cellular phone 50. A user can dial a number that is routed to a PBX switch 52. The PBX switch 52 can route the call to a server 54. The server 54 may include a database of robots and associated phone numbers and direct the call to the appropriate robot. The server database may include a caller ID field and cause a caller ID message to be sent to the robot. By way of example, the robot monitor may display a caller ID "Dr. Smith is calling". The caller ID may include a picture of the caller. The communication link between the robot 12 and the PBX 52 may be conducted in accordance with the Session Initiation Protocol ("SIP"). The link may only allow audio communication between the robot 12 and the cellular phone 50. Alternatively, if phone 50 is a "smart phone" and capable of video input and/or display, the link may allow both video and audio to be transmitted between the phone 50 and robot 12.

The video resolution of the cellular phone 50 is typically lower than the resolution of a computer monitor. The cellular phone 50 may transmit its video resolution to the robot 12. The robot 12 can compensate by either adjusting the resolution of the camera 38 or varying the resolution of the image after it is captured by the camera 38. The video transmitted from the robot 12 to the cellular phone 50 has a resolution that is consistent with the phone resolution.

The remote control station 16 may be a laptop or personal computer that has a cellular transceiver (not shown). When accessing a robot 12, the control station 16 may establish both a cellular link and a LAN link. By way of example, the cellular link may be in accordance with 3G protocol and the LAN link may operate under 802.11g. A first type of data may be sent through the cellular link and a second type of data may be transmitted with the LAN link. For example, video may be transmitted with the cellular link and audio may be sent through the LAN link. Some types of data may be sent through both links. For example, a stethoscope (not shown) may be connected to the robot and audio data of a heart beat is sent back to the control station through both the cellular and LAN links. This ensures the most rapid and robust delivery of data, which is particularly important given that delayed stethoscope audio may create false heart anomaly sounds, or mask heart anomalies. The control station can monitor one or more network parameters such as latency, packet loss and/or jitter. Unacceptable parameter values on one link may cause the station 16 to switch certain categories of data to the other link.

Figure 2:
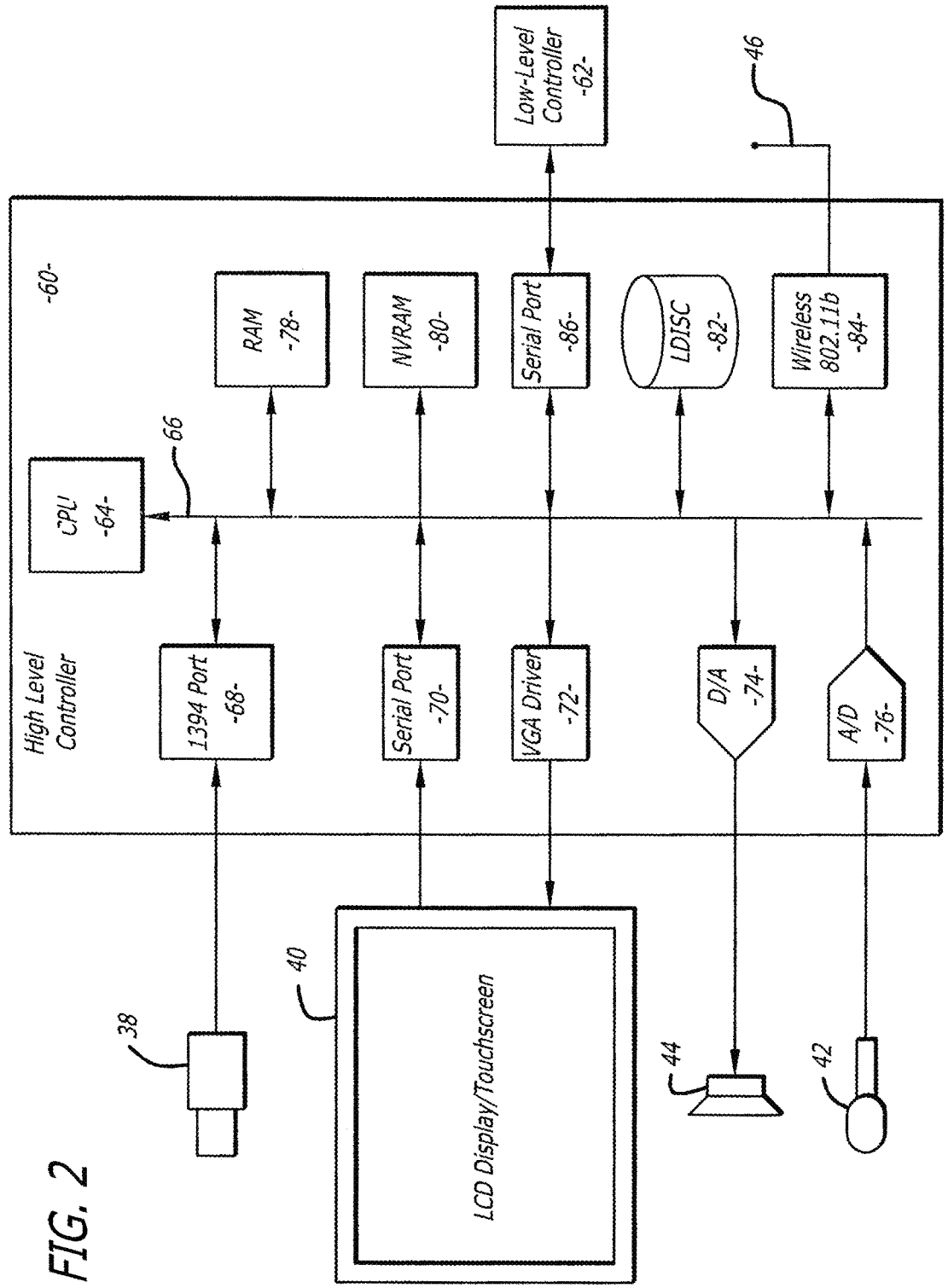
FIG. 2 is a schematic of an electrical system of a robot.
Figure 3:
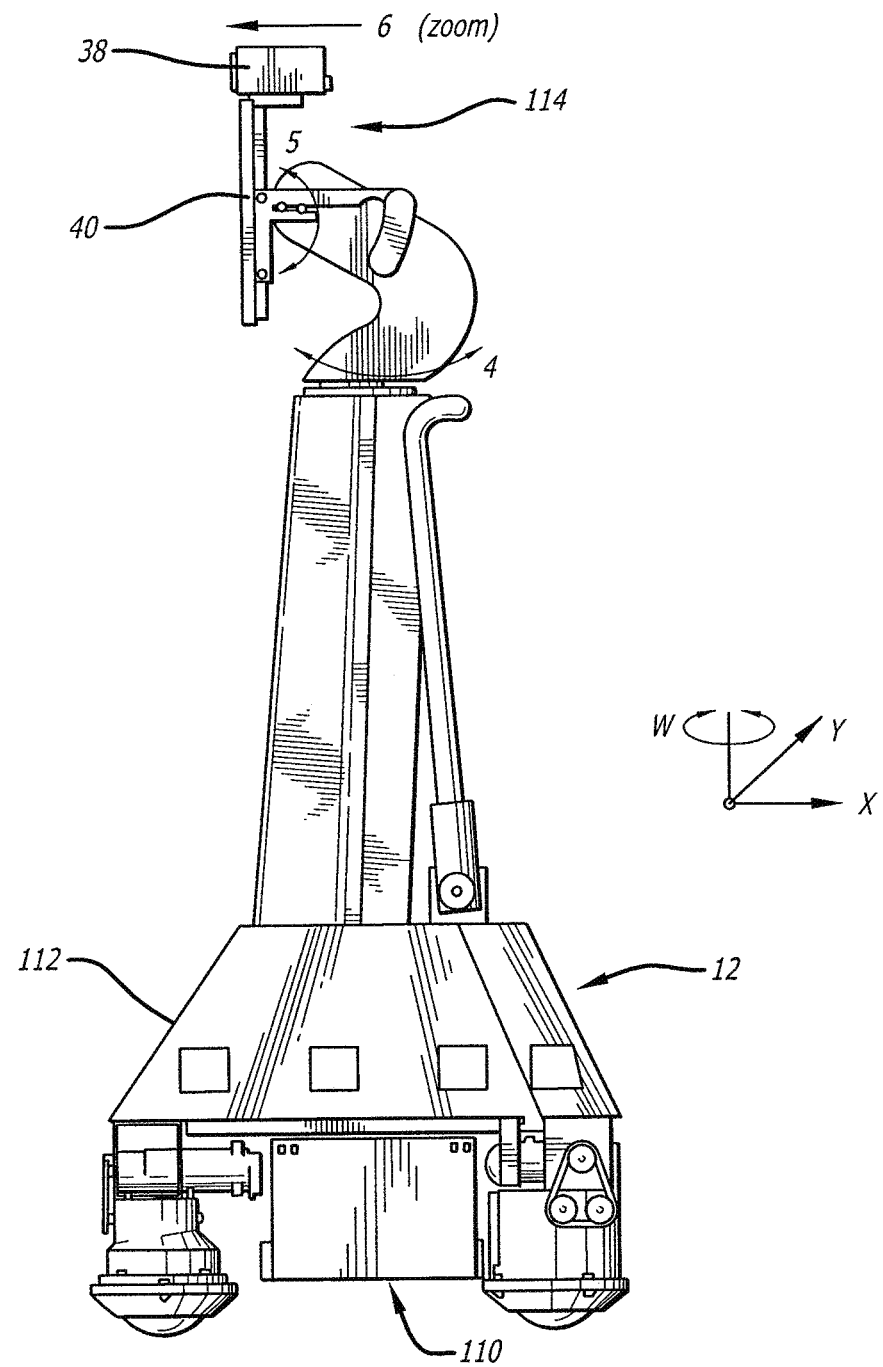
FIG. 3 is side view of the robot.

FIGS. 2 and 3 show an embodiment of the robot 12. The robot 12 may include a high level control system 60 and a low level control system 62. The high level control system 60 may include a processor 64 that is connected to a bus 66. The bus is coupled to the camera 38 by an input/output (I/O) port 68, and to the monitor 40 by a serial output port 70 and a VGA driver 72. The monitor 40 may include a touchscreen function that allows the patient to enter input by touching the monitor screen.

The speaker 44 is coupled to the bus 66 by a digital to analog converter 74. The microphone 42 is coupled to the bus 66 by an analog to digital converter 76. The high level controller 60 may also contain random access memory (RAM) device 78, a non-volatile RAM device 80 and a mass storage device 82 that are all coupled to the bus 72. The mass storage device 82 may contain medical files of the patient that can be accessed by the user at the remote control station 16. For example, the mass storage device 82 may contain a picture of the patient. The user, particularly a health care provider, can recall the old picture and make a side by side comparison on the monitor 24 with a present video image of the patient provided by the camera 38. The robot antennae 46 may be coupled to a wireless transceiver 84. By way of example, the transceiver 84 may transmit and receive information in accordance with IEEE 802.11.

The controller 64 may operate with a LINUX OS operating system. The controller 64 may also operate MS WINDOWS along with video, camera and audio drivers for communication with the remote control station 16. Video information may be transceived using MPEG CODEC compression techniques. The software may allow the user to send e-mail to someone at the robot site and vice versa, or allow someone at the robot site to access the Internet. In general the high level controller 60 operates to control the communication between the robot 12 and the remote control station 16.

The high level controller 60 may be linked to the low level controller 62 by serial port 86. The low level controller 62 runs software routines that mechanically actuate the robot 12. For example, the low level controller 62 provides instructions to actuate the movement platform to move the robot 12. The low level controller 62 may receive movement instructions from the high level controller 60. The movement instructions may be received as movement commands from the remote control station. Although two controllers are shown, it is to be understood that the robot 12 may have one controller controlling the high and low level functions.

FIG. 3 shows an embodiment of the robot 12. The robot 12 may include a holonomic platform 110 that is attached to a robot housing 112. The holonomic platform 110 provides three degrees of freedom to allow the robot 12 to move in any direction.

The robot 12 may have a head 114 that supports the camera 38 and the monitor 40. The head 114 may have two degrees of freedom (W, X and y) so that the camera 26 and monitor 24 can swivel and pivot as indicated by the arrows.

The system may be the same or similar to a robot system provided by the assignee InTouch Technologies, Inc. of Goleta, Calif. under the trademark RP-7. The system may also be the same or similar to the system disclosed in U.S. Pat. No. 6,925,357 issued Aug. 2, 2005, which is hereby incorporated by reference.

In operation, the robot 12 may be placed in a home, public or commercial property, or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home, property or facility by manipulating the input device 32 at a remote station 16.

The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

Message packets may be transmitted between a robot 12 and a remote station 16. The packets provide commands and feedback. Each packet may have multiple fields. By way of example, a packet may include an ID field a forward speed field, an angular speed field, a stop field, a bumper field, a sensor range field, a configuration field, a text field and a debug field.

The identification of remote users can be set in an ID field of the information that is transmitted from the remote control station 16 to the robot 12. For example, a user may enter a user ID into a setup table in the application software run by the remote control station 16. The user ID is then sent with each message transmitted to the robot.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables 1 and 2, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user<br>Notify requesting user that system is in use<br>Set timeout | Warn current user of pending user<br>Notify requesting user that system is in use<br>Set timeout = 5 m | Warn current user of pending user<br>Notify requesting user that system is in use<br>Set timeout = 5 m<br>Call back | Warn current user of pending user<br>Notify requesting user that system is in use<br>No timeout<br>Call back |
| | Caregiver | Warn current user of pending user.<br>Notify requesting user that system is in use.<br>Release control | Not Allowed | Warn current user of pending user<br>Notify requesting user that system is in use<br>Set timeout = 5 m<br>Queue or callback | Warn current user of pending user<br>Notify requesting user that system is in use<br>Set timeout = 5 m | Warn current user of pending user<br>Notify requesting user that system is in use<br>No timeout<br>Callback |
| | Doctor | Warn current user of pending user<br>Notify requesting user that system is in use<br>Release control | Warn current user of pending user<br>Notify requesting user that system is in use<br>Set timeout = 5 m | Warn current user of pending user<br>Notify requesting user that system is in use<br>No timeout<br>Callback | Notify requesting user that system is in use<br>No timeout<br>Queue or callback | Warn current user of pending user<br>Notify requesting user that system is in use<br>No timeout<br>Callback |
| | Family | Warn current user of pending user<br>Notify requesting user that system is in use<br>Release Control | Notify requesting user that system is in use<br>No timeout<br>Put in queue or callback | Warn current user of pending user<br>Notify requesting user that system is in use<br>Set timeout = 1 m | Warn current user of pending user<br>Notify requesting user that system is in use<br>Set timeout = 5 m<br>Queue or callback | Warn current user of pending user<br>Notify requesting user that system is in use<br>No timeout<br>Callback |

TABLE II-continued

| | Requesting User | | | | |
|---|---|---|---|---|---|
| | Local | Caregiver | Doctor | Family | Service |
| Service | Warn current user of pending user<br>Notify requesting user that system is in use<br>No timeout | Notify requesting user that system is in use<br>No timeout<br>Callback | Warn current user of request<br>Notify requesting user that system is in use<br>No timeout<br>Callback | Warn current user of pending user<br>Notify requesting user that system is in use<br>No timeout<br>Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

Figure 4:
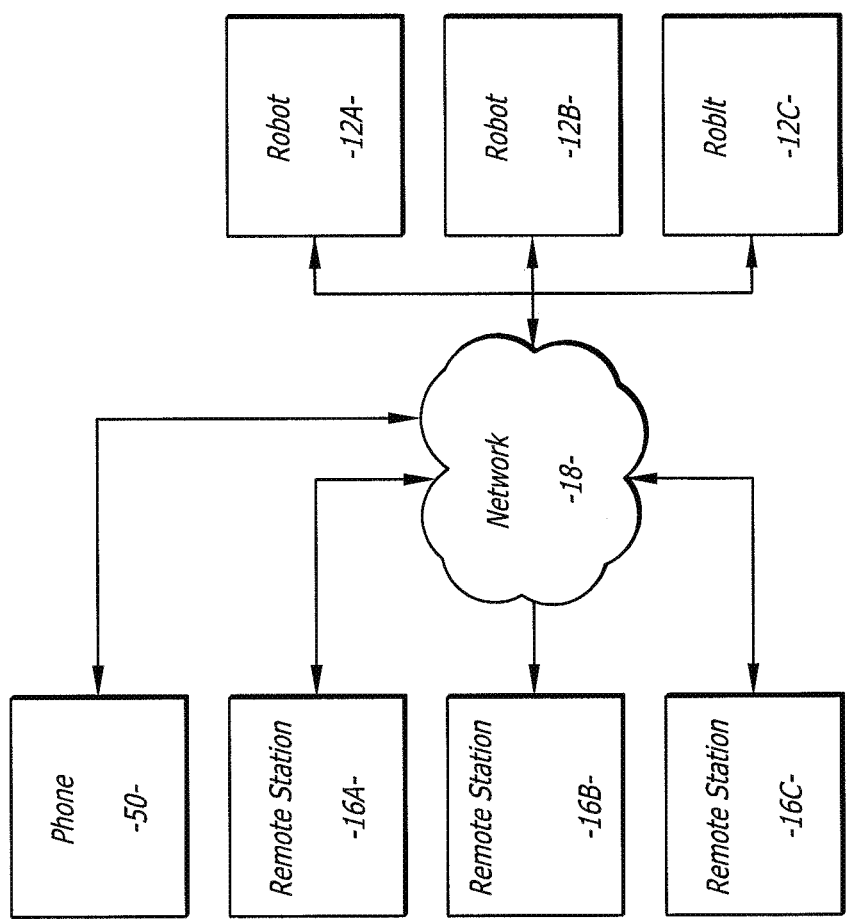
FIG. 4 is a schematic of a robotic system wherein a robot can be coupled to one or more remote stations and/or one or more robots.

FIG. 4 shows a system with a plurality of remote stations 16A, 16B and 16C, and a cellular phone 50 that can access one or more robots 12A, 12B and 12C through the network 18. The system also allows one robot to access other robots. The system can be set into an observation mode wherein a master remote station 16A controls movement of the robot and receives both video and audio information from the robot camera and speaker, respectively. The observer stations 16B and 16C and phone 50 may also receive audio and visual information transmitted between the robot 12 and the station 16A. This mode allows multiple users at stations 16B and 16C and phone 50 to observe use of the robot while a teacher or master at station 16A moves the robot. The session may be initiated in audio-only mode by phone 50, after which station 16A with camera, display and joystick may be invited to join, and station 16A takes master control.

During a session the master remote station 16A can retransmit the audio/visual information received from the robot 12 to the observer stations 16B and 16C and phone 50. This can be done by changing the ID(s) in the ID field of the data packets received from the robot and then retransmitting the packets to the observer stations. Alternatively, the master remote station 16A can instruct the robot to transmit the audio and visual information to the master 16A, the observer 16B and 16C remote stations and phone 50. It being understood that each remote station 16A, 16B and 16C, and phone 50, has a unique network identifier that allows the robot to direct information to each station. The packets may contain a BROADCAST field that contains the station IDs for the remote stations that are to receive packets from the robot. The BROADCAST field may be filled by the master station 16A.

The session mode allows for training through the robot. For example, the master remote station 16A may be operated by a physician who moves the robot into visual and audio contact with a patient. The observer remote stations 16B an 16C and phone 50 may be manned by personnel such as interns that observe and receive instructional training on providing care giving to the patient. Although instruction of medical personnel is described, the system can be used to train any group of users that are remotely located from a training area. For example, the system may be used to train personnel at a department store or allow potential buyers of real estate property to remotely view the property.

Another session can occur as follows. The robot 12 may be in the vicinity of a patient. A doctor may not have ready access to a control station but does possess a cellular phone.

The doctor calls into the robot to establish audio communication with the patient and any other medical personnel at the robot site. The doctor can then walk to a control station and establish both audio and video communication with the patient through the robot and station. The control station joystick also allows the doctor to control movement of the robot. The server can sense that the same doctor is accessing the robot through the control station and terminate then back to the doctor's phone.

Figure 5:
FIG. 5 is an illustration of a user interface session prompt.

The doctor may seek the input of another doctor such as a cardiologist. The doctor may call or text the cardiologist from the cellular phone. The cardiologist may have a videoconferencing capability. The cardiologist may enter and navigate the system until presented with the display shown in FIG. 5. The display provides a list of various robotic teleconferencing sessions 120. The cardiologist highlights the desired sessions and selects the graphical CONNECT NOW button 122. The cardiologist is then provided access to video and audio in the session. The cardiologist's image may be displayed by the robot monitor.

Figure 6:
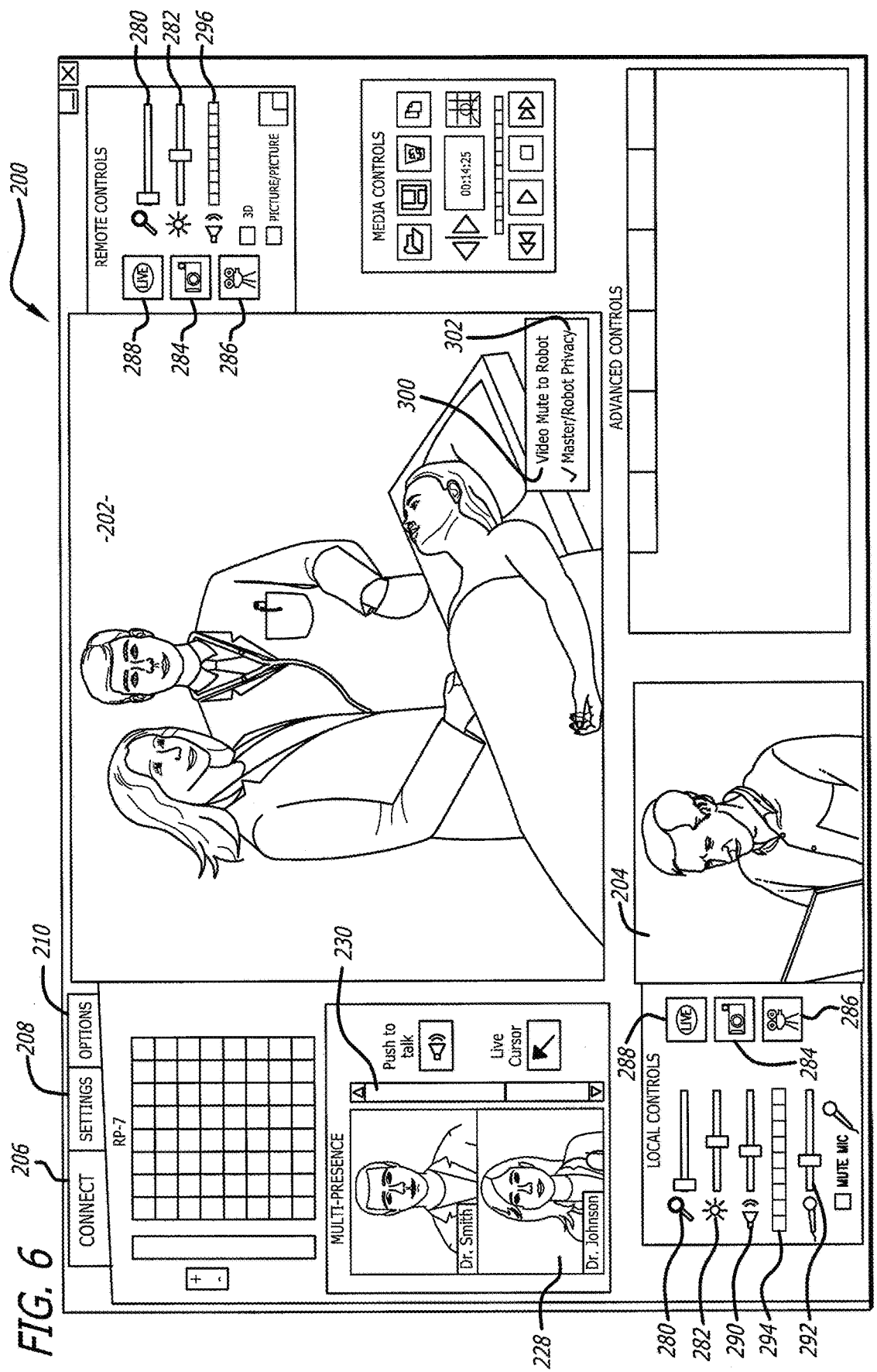
FIG. 6 is an illustration of a user interface.

FIG. 6 shows a display user interface ("DUI") 200 displayed at the master control station 16A. The DUI 200 may include a robot view field 202 that displays a video image captured by the camera of the robot. The DUI 200 may also include a station view field 204 that displays a video image provided by the camera of the master remote station 16A. The DUI 200 may be part of an application program stored and operated by the computer 22 of the remote station 16A.

The DUI 200 may include a "Connect" button 206 that can be selected to connect the station to a robot. Selection of the Connect button 206 may cause the display of pull-down screens, etc. that allow the user to select a desired robot. System settings and options can be selected through buttons 208 and 210, respectively.

Figure 7:
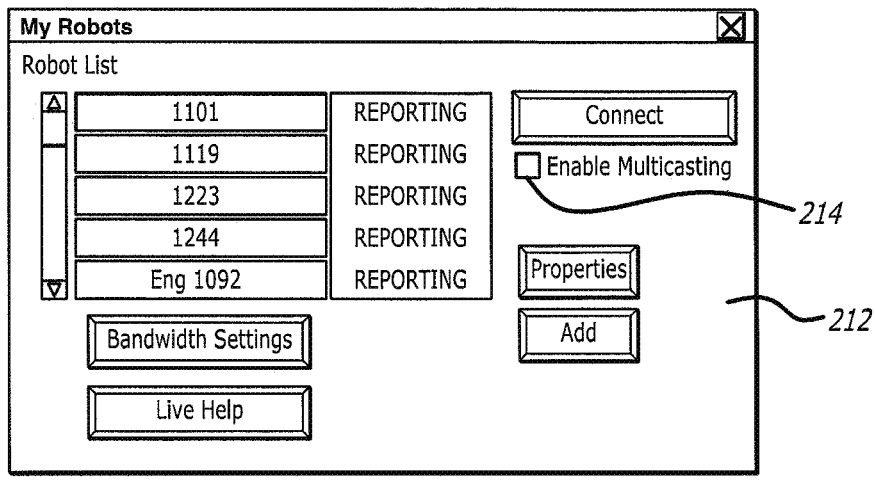
FIG. 7 is an illustration of a message popup of the user interface.

One of the options is to allow for multicasting. FIG. 7 shows a menu 212 with an "Enable Multicasting" box 214 that can be "checked" to allow for other remote station and/or phone to join a multi-cast session. The other stations/phone may have audio only, video only, or both video and audio communication.

Figure 8A:
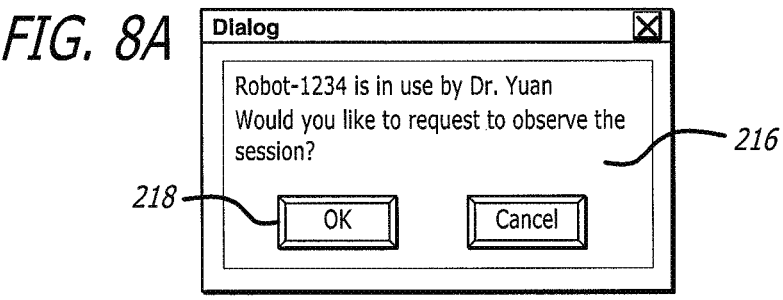
FIGS. 8A-C are illustrations of graphical messages.
Figure 8B:
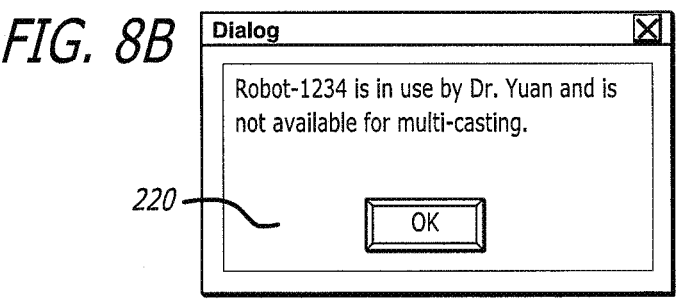
Figure 8C:
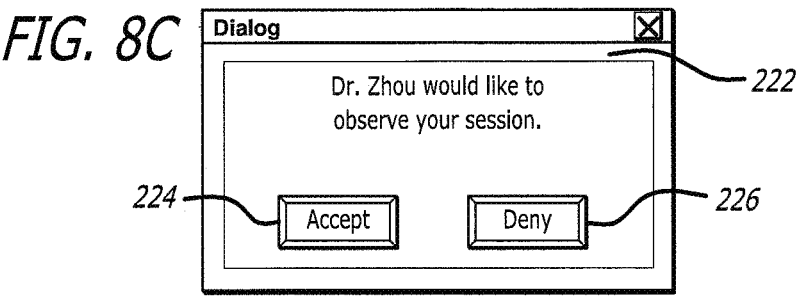

A user at an observer station may attempt a connection with the same robot. If a robot is already in use the screen may display a message box 216 as shown in FIG. 8A. The message box 216 includes an "OK" button 218 that allows the user to request joining the session as an observer. If the user presently connected to the robot has not enabled the multicasting feature then a message 220 may be displayed indicating this fact as shown in FIG. 8B. If the user selected the OK button 218 then the master user may receive the message 222 shown in FIG. 8C. The message includes an "Accept" button 224 and a "Deny" button 226 that allows the master user to accept or deny the request to observe the session, respectively. When an observer is accepted the observers may receive the audio/video feeds from by the robot.

User's that are accepted are displayed in an observer view field 228 of the master control station DUI 200 shown in FIG. 6. The field 228 can provide video images of the users captured by the cameras of the observer remote control stations. Each video image may also include a caption of the observer's name. The field includes a scroll down tab 230 that allows the master user to scroll down the video images of the observers.

Figure 9:
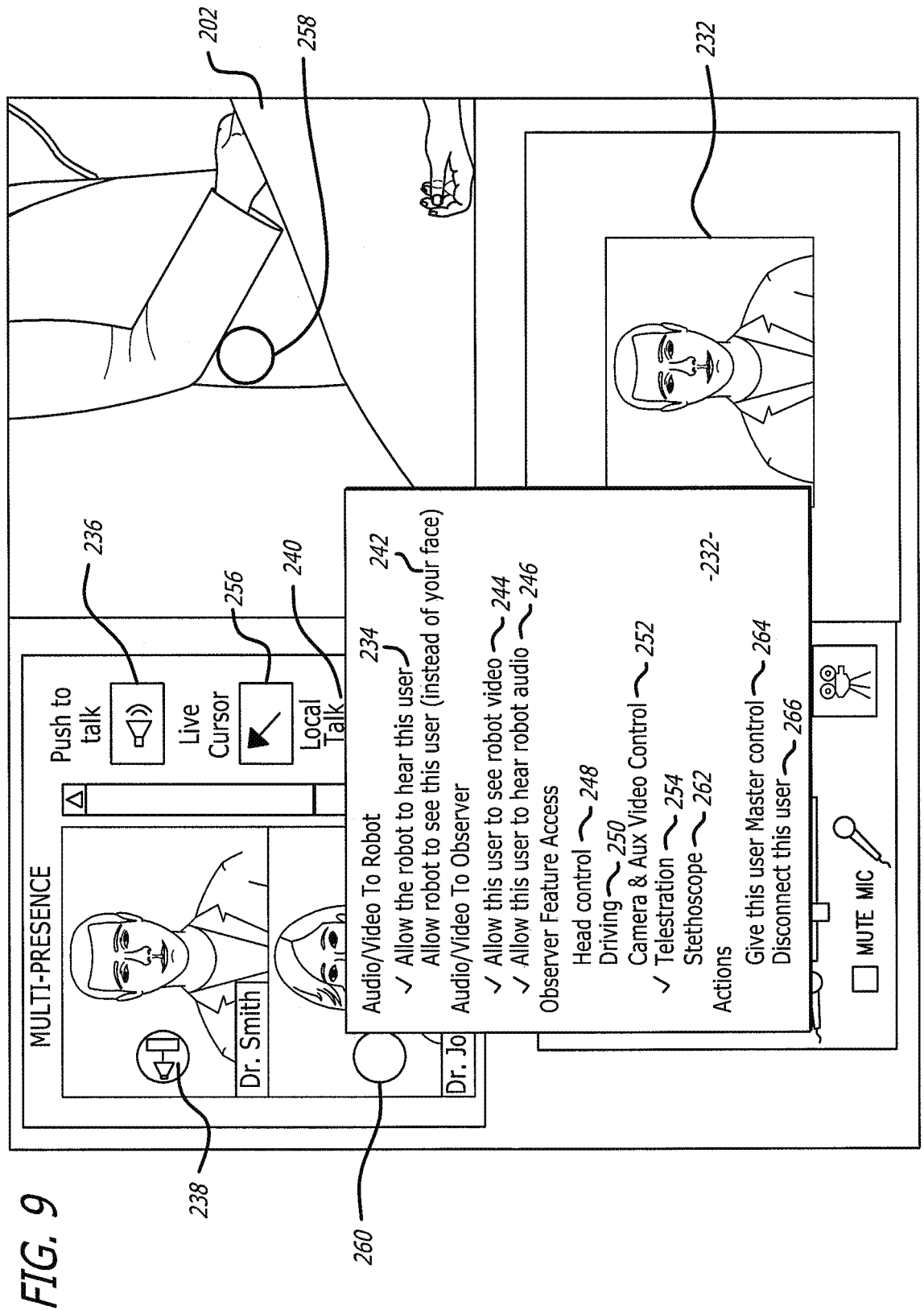
FIG. 9 is an illustration of the user interface shown in FIG. 6 with a pull-down menu.

The master user can right click on any observer video image to display the pull down menu 232 shown in FIG. 9. The pull down menu 228 allows the master user to select various options for the selected observer. The pull down menu 232 includes an "Allow The Robot To Hear This User" feature 234 that can be selected so that the observer can provide audio to the robot. The system may allow for simultaneous three way audio between the robot, master user and one observer. Both the master and the observer stations include a "Push To Talk" icon 236. If there is more than one observer then the "Push To Talk" icon 236 is enabled and the observer must continuously select the icon 232 to talk, much like a walkie-talkie button. The space bar may also be pushed after the icon 236 is selected to allow audio communication to the robot. When Push To Talk is selected then an icon 238 can be displayed in the observers video image to indicate which observer is providing audio input to the robot. The master and observer stations may also have a "Local Talk" icon 240. Selecting the Local Talk icon allows for textual communication between just the remote stations, popping up a text chat dialog box within each interface, which allows the master and observers to exchange text messages. Prior to displaying the text chat dialog box, a popup dialog box (not shown) may be displayed to the user who initiated Local Talk, which would list all current session participants, and allow the user to select only those participants to be part of the Local Talk. There may be a "Limit Voice" box (not shown) that can be selected to limit audio output of participants in the local chat to only those other remote stations participating in the local chat.

An "Allow Robot To See This User" feature 242 can be selected so that the observer's video image is provided to the monitor of the robot instead of the master user's video image. The observer's video image may be displayed in the station view field 204 when that observer's image is provided to the robot. The "Allow This User To See Robot Video" 244 and "Allow This User To Hear Robot Audio" features 246 can be selected so that the observer receives the video and audio feeds from the robot, respectively.

The "Head Control" feature 248 allows the selected observer to control the robot head to move the robot camera. The "Driving" feature 250 allows the observer to drive the robot. When the Driving feature is selected robot data such as position sensor data, battery power, etc. are provided to the selected observer's remote station. The "Camera & Aux Video Control" feature 252 allows the observer to control robot camera functions such as zoom, brightness, etc. The master no longer has the head, driving and camera controls when these features are transferred to an observer.

The menu 232 includes a "Telestration" feature 254 that allows an observer to annotate an image provided by to robot. For example, the image can be a document or an X-ray. An observer can annotate the image, for example to circle and area of the X-ray to help communicate with a patient at the robot site. The master or any observer can enable a cursor function by selecting a "Live Cursor" icon 256. Selecting the icon 256 allows the user to move a cursor 258 that is overlayed on the robot video image. The cursor 258 is provided on the image field 202 for all remote stations in a session. The master and observers can each be designated a different color so that different cursors can be distinguished by the users. The cursor color 260 can be displayed in the video image of the master or the observer.

The robot may connected to a medical instrument such as a stethoscope. The "Stethescope" feature 262 of the pull down menu 232 allows the observers to receive instrument input from the stethoscope. The menu 232 may have a "Give This User Master Control" feature 264 that allows the selected observer to become a master user. The master can also disconnect an observer by selecting the "Disconnect This User" feature 266.

Figure 10:
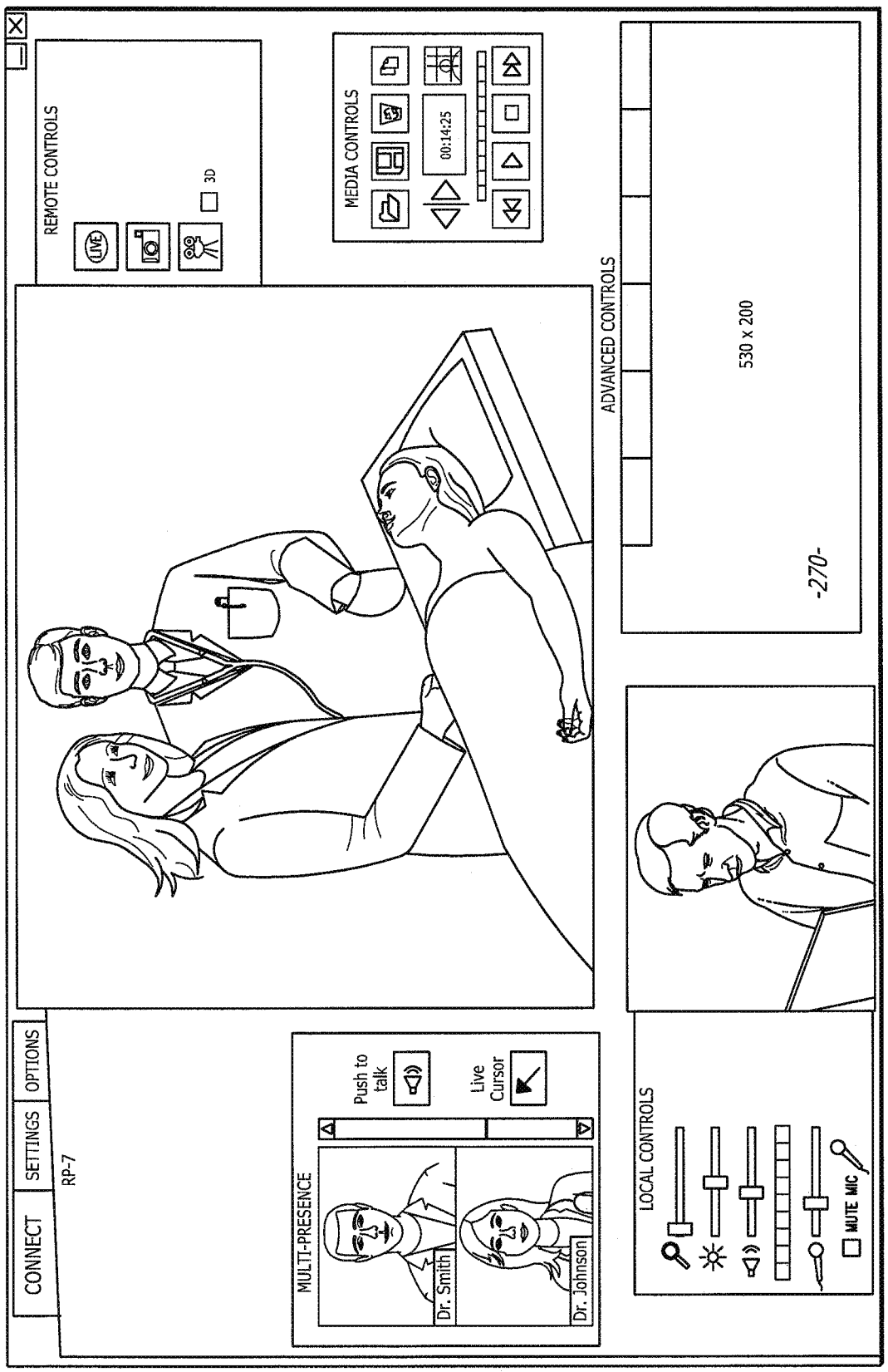
FIG. 10 is an illustration showing a user interface for an observer remote control station.

FIG. 10 shows a user interface 270 for an observer. The interface does not include robot control functions unless enabled by the master user. The interface 270 is similar to the master DUI 200, but lacks certain robot controls.

Referring again to FIG. 6, both the robot view field 202 and the station view field 204 may have associated graphics to vary the video and audio displays. For example, each field may have graphical slide bars 280 and 282 to vary the zoom and brightness of the cameras, respectively. A still picture may be taken at either the robot or remote station by selecting one of the graphical camera icons 284. The still picture may be the image presented at the corresponding field 202 or 204 at the time the camera icon 284 is selected. Capturing and playing back video can be taken through graphical icons 286. A return to real time video can be resumed, after the taking of a still picture, captured video, or reviewing a slide show, by selecting a graphical LIVE button 288.

Figure 11:
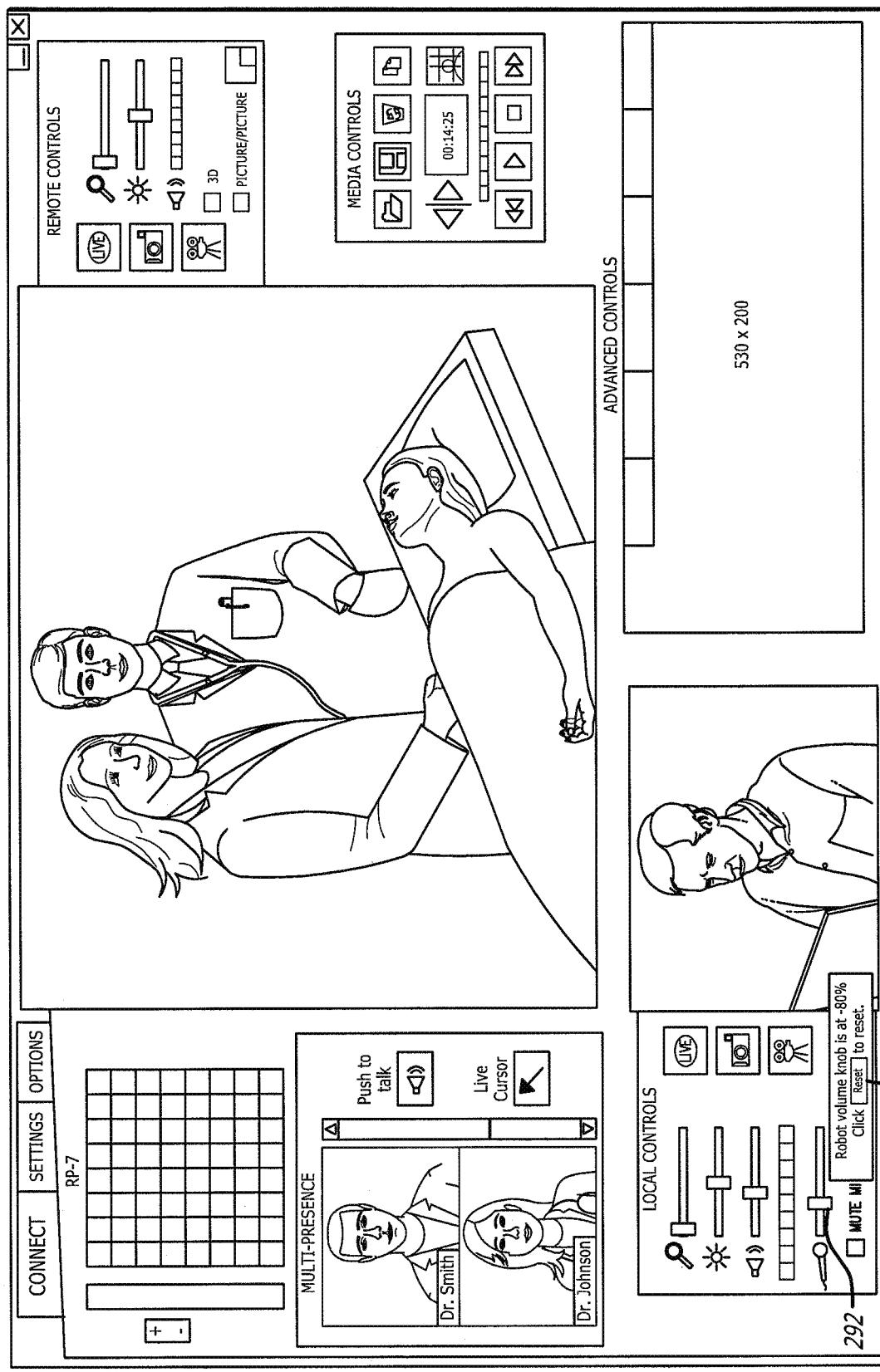
FIG. 11 is an illustration similar to FIG. 5 showing microphone volume control features.

The local controls can include slide bars for the local station speaker 290 and microphone 292. Also displayed is a microphone meter icon 294 that varies with the volume of the user's voice. The robot volume may be different from the user's input volume. The remote controls also includes a microphone meter icon 296 that represents the user's audio volume at the robot. The robot may have a local volume control so that user's at the robot site can vary the robot speaker volume. Normally the meter icons 294 and 296 will represent essentially the same value. The robot volume may be different from the user's input volume, for example, if the robot local volume control is adjusted the at the robot site. As shown in FIG. 11, if this occurs the volume slide bar 292 may be enabled to allow the user to vary the microphone. The DUI may also display a "Reset" button 298 that can be selected to automatically reset the robot speaker volume to a center position.

Referring to FIG. 6, the robot view field 202 may include a "Video Mute To Robot" feature 300 which when selected prevents audio and video transmission to the robot from all remote stations. Field 202 may also have a "Master/Robot Privacy" feature 302 that can prevent the observer stations from receiving robot video and audio from both the robot and the master control station.

Figure 12:
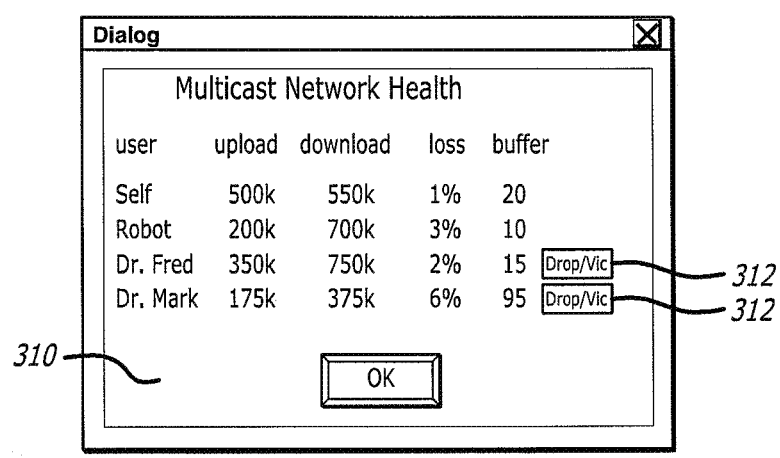
FIG. 12 is an illustration of a dialog box showing bandwidth requirement of the system during a session.

The master user can also be allowed to control the bandwidth of the system by controlling the video feeds to the observer stations. FIG. 12 shows a dialog box 310 that displays the bandwidth usage of various participants in a session, along with network health parameters such as packet losses and jitter between participants. "Drop Vid" buttons 312 may be placed next to observer stations so that the master user can drop a particular observer's video.

Figure 13:
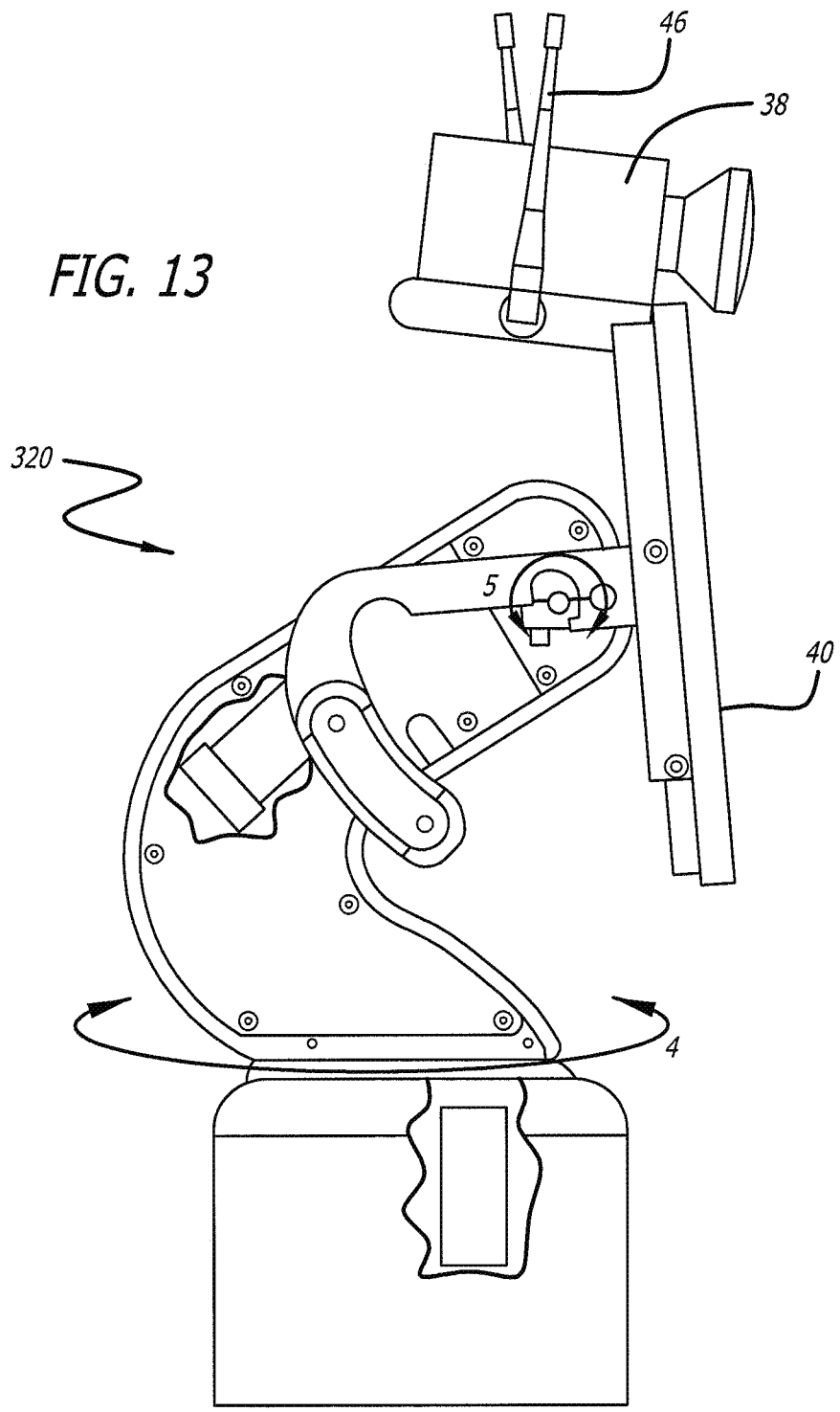
FIG. 13 is a side view of a robot head.

FIG. 13 shows a non-mobile robot head 320 that can both pivot and spin the camera 38 and the monitor 40. The robot head 320 can be similar to the robot 12 but without the platform 110. The robot head 320 may have the same mechanisms and parts to both pivot the camera 38 and monitor 40 about a pivot axis 4, and spin the camera 38 and monitor 40 about a spin axis 5. The pivot axis may intersect the spin axis. Having a robot head 320 that both pivots and spins provides a wide viewing area. The robot head 320 may be in the system either with or instead of the mobile robot 12.

Figure 14:
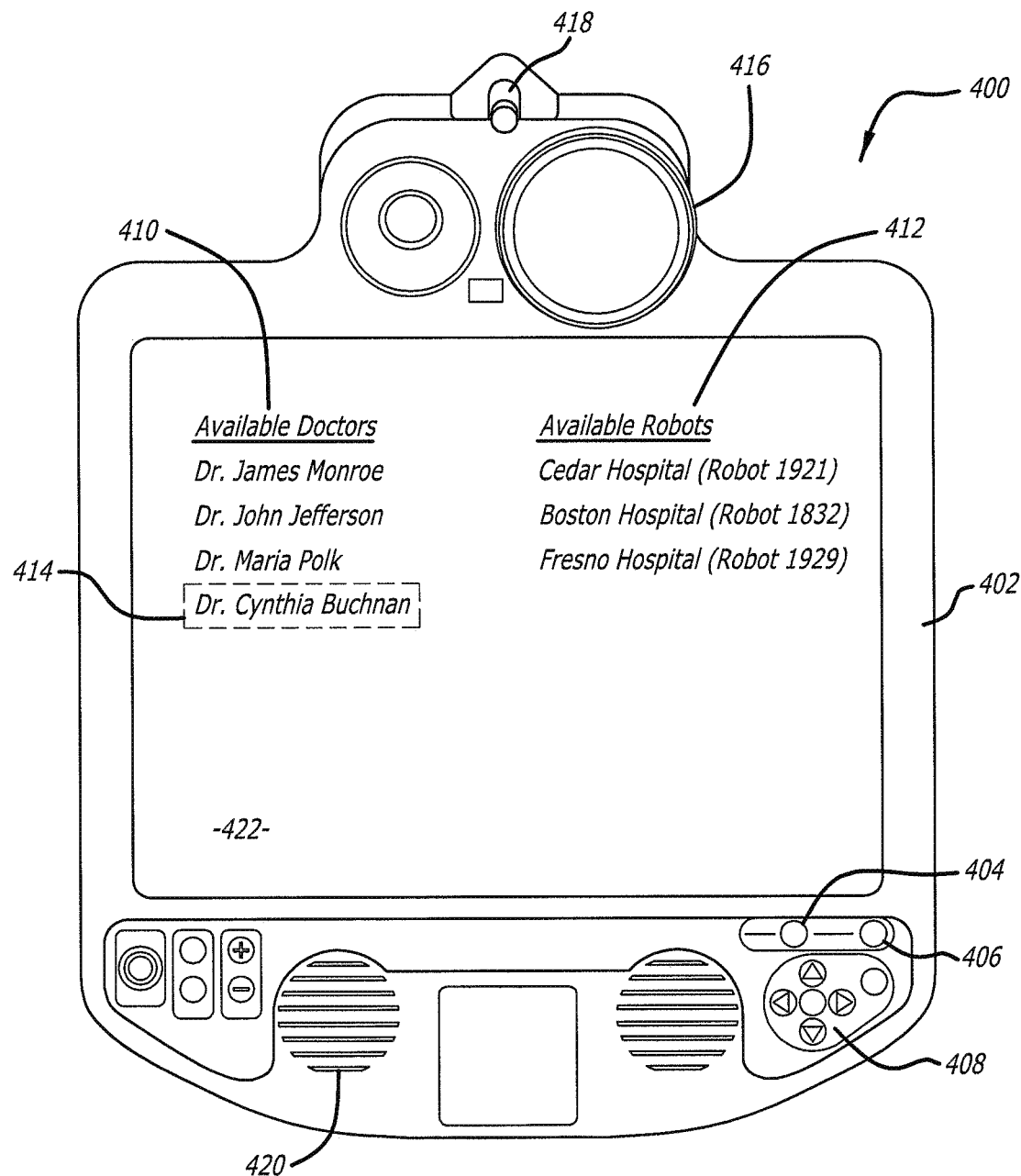
FIG. 14 is a front view showing a user interface of a robot head; and,
FIG. 15 is a front view of the robot head showing a connectivity prompt.

FIG. 14 shows a robot head 400 that has a user interface 402. The robot head 400 may be part of a robot with a mobile platform as shown in FIGS. 1 and 3, the head shown in FIG. 13, or some other robotic system. For example, the head 400 may be attached to a boom. The user interface 402 allows an operator at the robot site to initiate and control access to the head 400. The interface 402 may include a "Connect" button 404 and a "Disconnect" button 406, that allow a user to initiate and terminate access to the head 400, respectively. Menu buttons 408 may be located below the buttons 404 and 406.

The interface 402 may display a list of remote stations (Available Doctors) 410 and a list of robots (Available Robots) 412. The user can create a link with one or more remote station by manipulating the Menu buttons 408 and selecting a highlighted station 414. More than one remote station can be selected to create a multi-casting session. The user can create access to other robots by manipulating the Menu buttons 408 and selecting a highlighted robot. A multi-casting session may also be created with multiple robots by selecting multiple robots. By way of example, a doctor at the robot site may provide access to another doctor at another remote station. The doctor may also obtain access to another robot located at another hospital location. The interface 402 allows a user at the robot site to initiate a teleconferencing sessions. The head 400 includes a camera(s) 416, microphone 418, speakers 420 and monitor 422 to allow for two-way teleconferencing with one or more remote stations and/or on or more other robots. The head may also have a laser pointer 424 that emits a laser (not shown).

Figure 15:
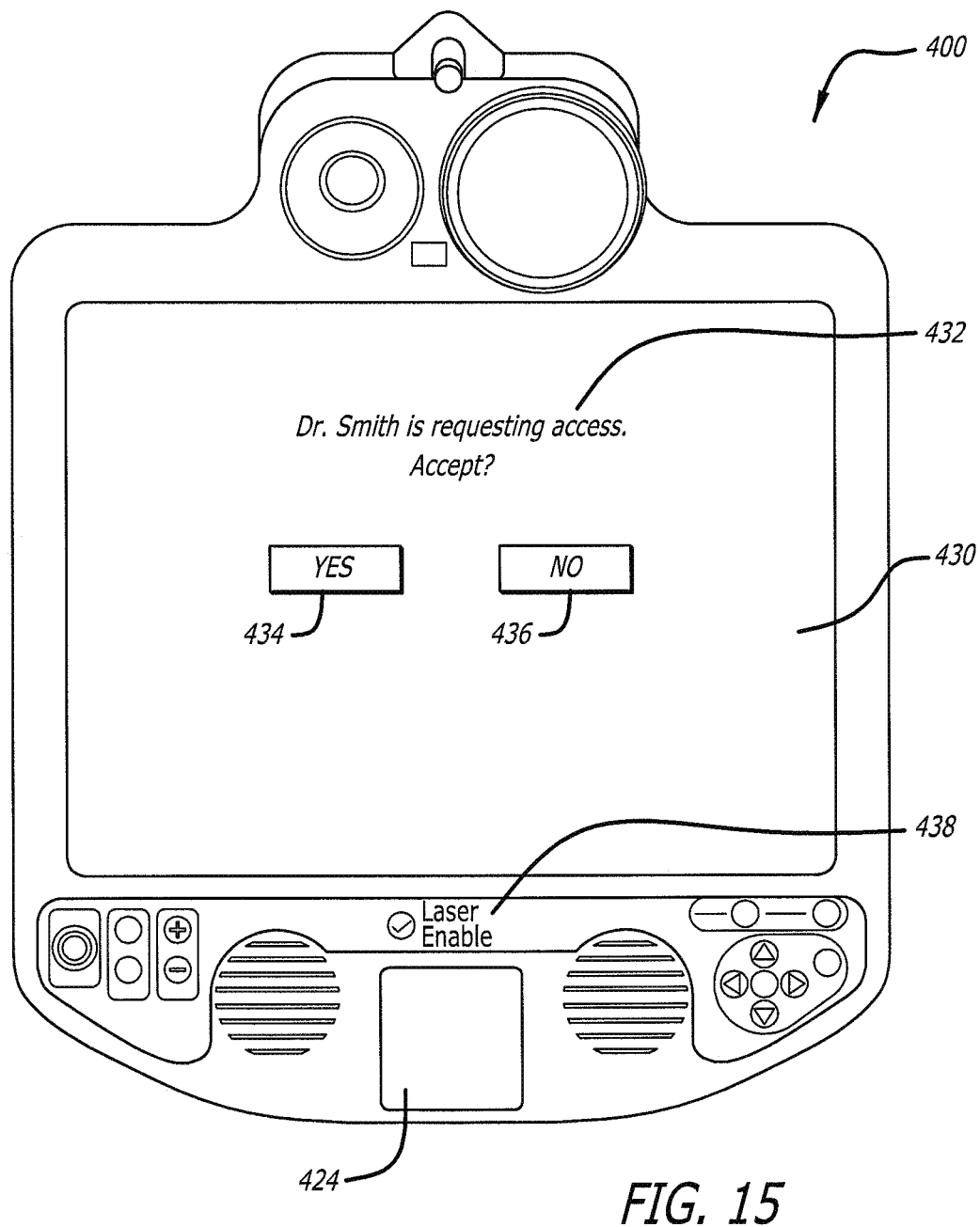

FIG. 15 shows the robot head 400 displaying a connectivity prompt 430. The prompt 430 may include a message 432 such as "DR. SMITH IS REQUESTING ACCESS. ACCEPT?" and YES 434 and NO 436 graphical buttons. The user of a remote station may select a graphical icon (not shown) that causes the connectivity prompt 430 to appear. Access to the head 400 is not granted until a user at the robot site selects the YES button 434 through the Menu buttons 408. Granting access may then allow the video and audio provided by the head to be transmitted to the remote station. Alternatively, audio may be provided when the prompt 430 is generated but before access is granted. Granting access then provides the remote station with the video feed from the head 400.

The head 400 may have a laser pointer 440 that can be used to point at objects, etc. The head 400 may include a Laser Enable button 438 that allows the user at the robot site to turn the laser pointer 424 on and off. The user at the robot site may disable the laser pointer, if for example, the laser creates a safety issue.

The system may have numerous applications. For example, a physician intensivist may initiate a remote presence session with a robot in order to diagnose a patient in an Emergency Room. Upon examining the patient, the physician may realize that the patient assessment will require consultation by a neurology specialist. The intensivist calls the neurologist by phone, asking him to join the session. Upon receiving the telephone request, the neurologist opens his laptop, selects the robot in question from the robot list in the interface, and clicks "Connect". Seeing the message in FIG. 8A, he clicks "OK" and then sees the message in FIG. 8B. The intensivist meanwhile sees the message in FIG. 8C and clicks "Accept". At this point the neurologist receives the robot video and can hear both the robot-side audio and the intensivist.

The intensivist uses the Live Cursor to point to the patient's face and EEG data on a wall. The neurologist obtains background information that can be provided by a nurse standing next to the patient and in front of the robot, as well as ICU-specific information provided by the intensivist on the master control station. Then, the neurologist can provide an audio assessment of the patient's condition. The intensivist then right-clicks on the thumbnail image of the neurologist in field 288, and clicks the appropriate features in the pull-down menu to allow the neurologist to be seen and heard on the robot. The neurologist can then inform both the patient and family of the condition.

In another application, a surgeon may be logged onto a robot and performing rounds in patient rooms within a hospital. Residents from hospitals in other cities join the session in the manner described above. The surgeon describes what he is doing to the residents, who may ask questions, and thereby learn the best way to round patients.

In another application, a hospital CEO may connect to the robot, and telephones three prospective doctors whom the hospital is courting to join the staff. These doctors each join the session as discussed above. The CEO then uses the joystick to drive the robot through the hospital, performing a virtual tour, and discusses the facility with the observer physicians.

In yet another application, a sales VP of an MRI manufacturing company may connect to a robot in the laboratory wing of a hospital, and then phones the COO of a different hospital to join the session. Upon joining, the sales VP drives the robot into the MRI lab and drives around the MRI machine, describing its features. An on-site MRI technician operates certain controls on the direction of the sales VP. The sales VP explains to the COO the various benefits of purchasing the MRI machine.

Figure 16:
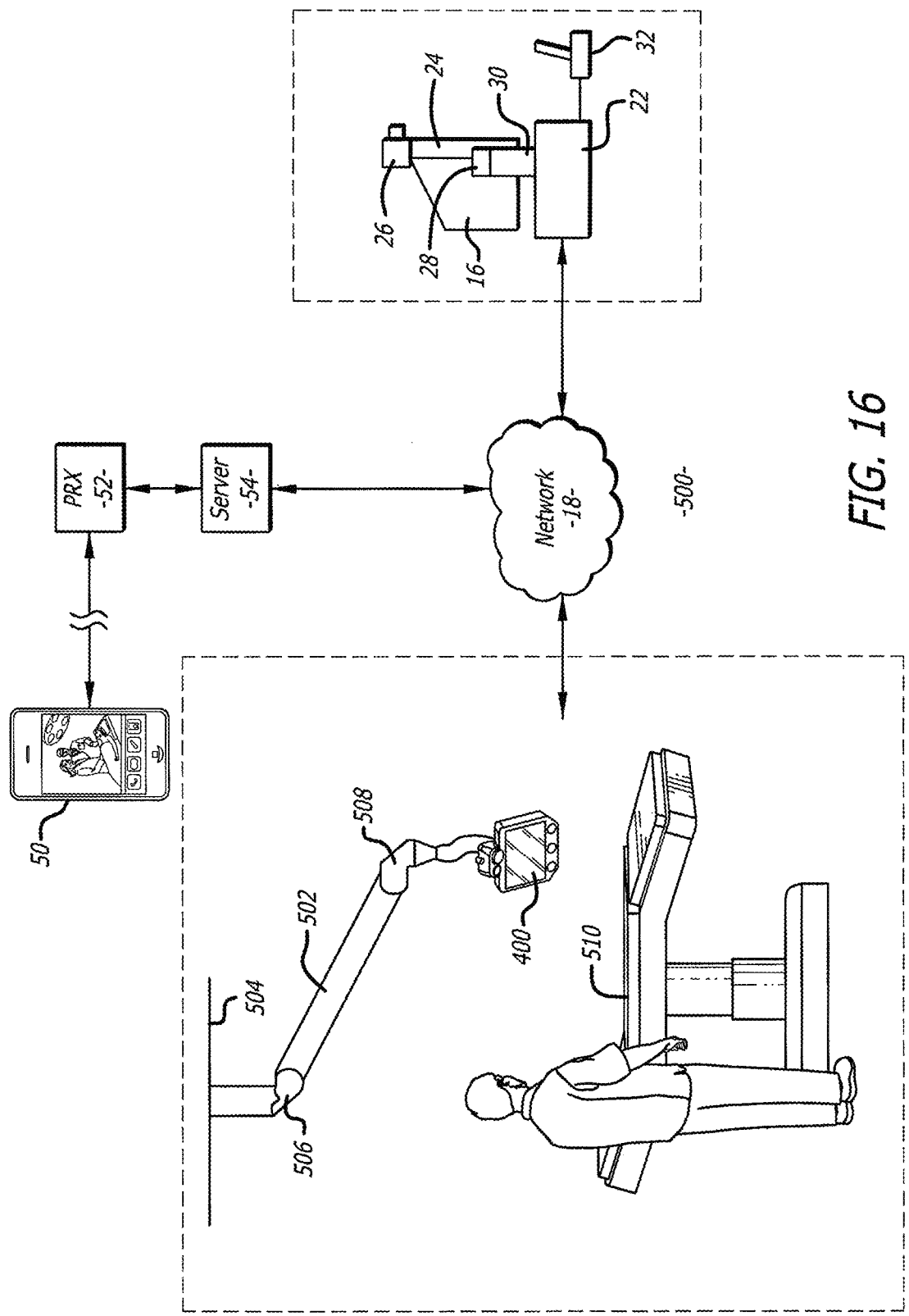
FIG. 16 is an illustration of an alternate embodiment of a tele-presence system.
Figure 17:
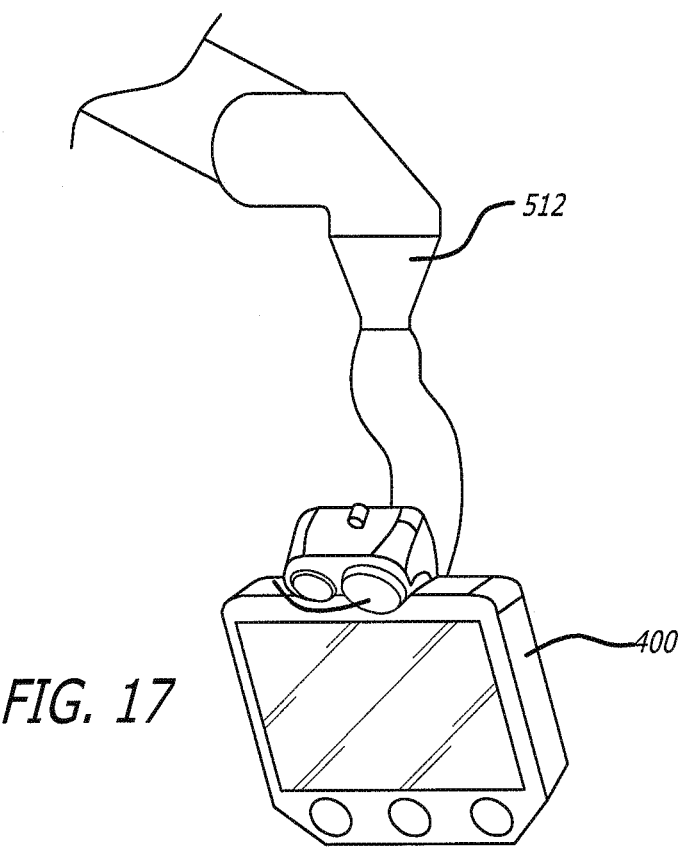
FIG. 17 is an enlarged view of a robot face of the system.
Figure 18:
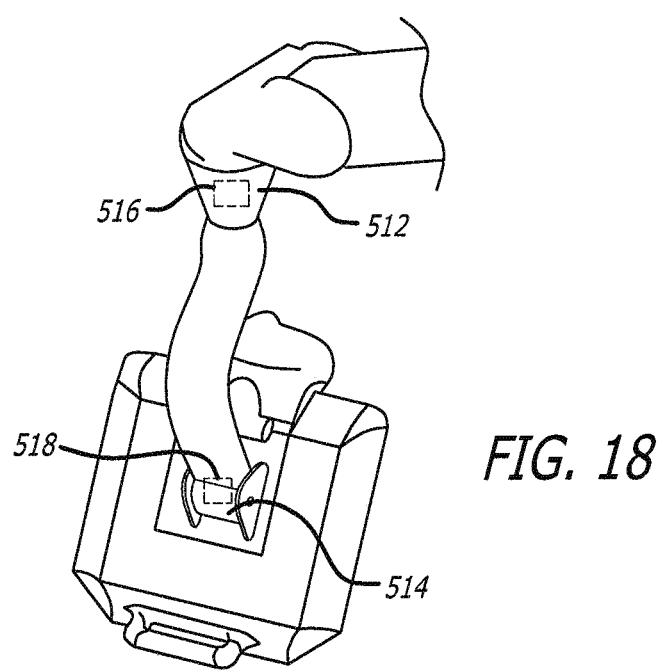
FIG. 18 is a rear view of the robot face.

FIGS. 16, 17 and 18 show another embodiment of a tele-presence system 500. The system 500 includes a robot face 400 attached to a boom 502. The boom 502 may extend from the ceiling 504 of a medical facility. The boom 12 may include articulate joints 506 and 508 that provide at least two degrees of freedom and allow a user to move the robot face 400 relative to a medical table 510 such as an operating room ("OR") table.

The boom 502 may have additional joints 512 and 514 that allow the robot face 400 to be panned and tilted, respectively. The joints 512 and 514 may contain actuators 516 and 518, respectively, that can be remotely actuated.

Figure 19:
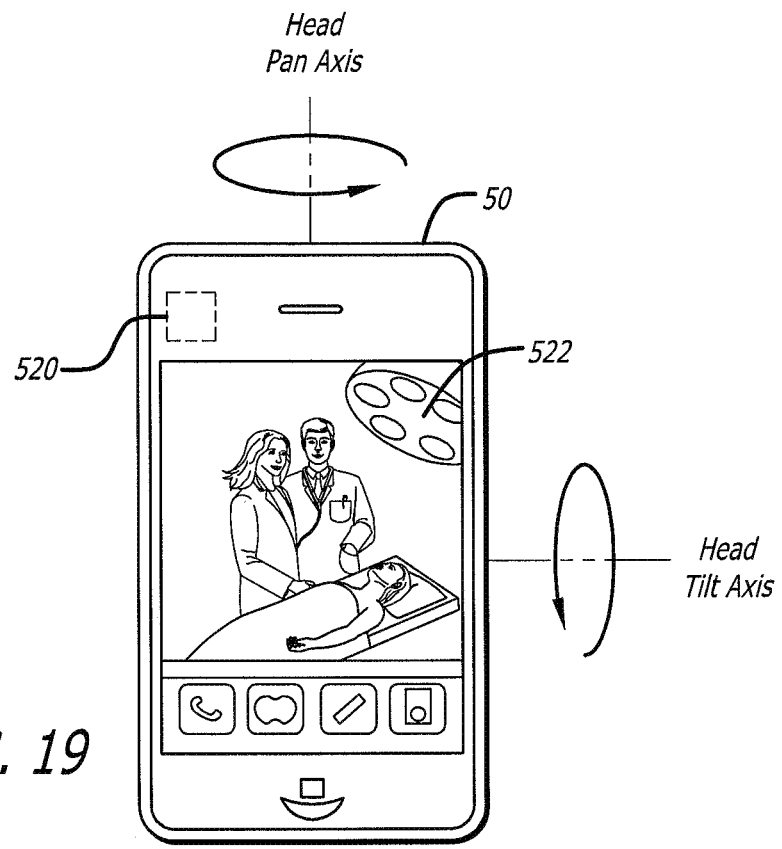
FIG. 19 is an illustration showing a phone that can be moved to activate a robot face.

As shown in FIG. 19 the cellular phone 50 may include an accelerometer 520 that can sense motion of the phone. The phone may transmit movement commands to the robot that are a function of the sensed movement of the cellular phone 50. For example, the user can move the phone about a Tilt Axis that will cause a corresponding tilt movement of the robot head. Likewise, the user may move the phone about a Spin Axis that induces a corresponding pan movement of the head. When the controlled robot is connected to an overhead boom, this control may allow the user looking down at phone 50 to control the robot head as if they were looking down from the ceiling above the robot head.

Figure 20:
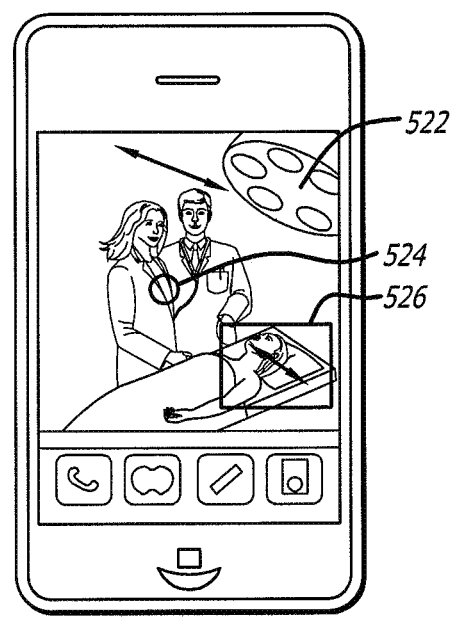
FIG. 20 is an illustration of the phone showing a cursor and zoom highlight box.

The phone 50 may include a touch screen 522 that causes robot movement that corresponds to the movement of a user's fingers. For example as shown in FIG. 20, the phone may display a cursor 524 that can be moved by having the user drag their fingers across the screen. Movement of the cursor 524 causes a corresponding movement of the robot and/or robot head. The user may use two fingers to rotate about the cursor to cause pan and tilt movement at the robot head. Touching a corner of an image may cause the presentation of a highlighted box 526. The highlighted box can be manipulated to cause the robot camera to zoom in or zoom out while simultaneously, in case of zooming in, pan and tilt the robot head to point in the direction of the center of the zoom. For example, the user can place two fingers on the box and either move their fingers apart to zoom in, or move the fingers together to zoom out.

The system 10 allows a system user such as a surgical specialist to view a patient on the table 40 and provide remote medical consultation through the remote station 16 and the robot face 14. Personnel at the surgical site can transmit questions and responses through the system back to the system operator. The robot camera 50 allows the specialist to view the patient and enhance the medical consultation. The robot monitor 52 can display the specialist to provide a feeling of presence at the surgical site. The boom 12 allows the personnel to move the robot face 14 into and out of the surgical area.

The robot face 14 can be retrofitted onto booms that presently exist in medical facilities. For example, some present medical facilities include a monitor attached to a boom. The existing monitor can be replaced with the robot face 14 that is then coupled to the remote station 16.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A robot system, comprising:
   a robot that includes a robot camera, a robot monitor, a robot microphone, and a robot speaker;
   a cellular phone in communication with said robot, said cellular phone includes an accelerometer that senses movement of said cellular phone, said cellular phone transmits movement commands to said robot that are a function of said movement sensed by said accelerometer, wherein the robot monitor moves in response to the movement commands.

2. The robot system of claim 1, further comprising a server that routes communication between said robot and said cellular phone.

3. The robot system of claim 1, wherein said cellular phone is in communication with said robot camera and provides information to said robot regarding a resolution of an image displayed by said cellular phone, said robot varies a resolution of said image captured by said robot camera to correspond with said cellular phone resolution.

4. The robot system of claim 1, wherein said robot moves in response to a touch screen command provided on said cellular phone.

5. The robot system of claim 1, wherein said robot camera enters a zoom mode in response to a touch screen command provided on said cellular phone.

6. The robot system of claim 1, further comprising a remote station that includes a monitor that displays an image captured by said robot camera while said cellular phone is in communication with said robot and said robot monitor displays the image captured by a camera of the cellular phone.

7. The robot system of claim 1, wherein said remote station is connected to said robot through a first communication link and a second communication link.

8. The robot system of claim 7, wherein first data is provided on said first communication link and second data is provided on said second communication link.

9. The robot system of claim 8, wherein said remote station monitors at least one communication parameter and switches the first data to the second communication link or the second data to the first communication link.

* * * * *